US005750732A

United States Patent [19]

Verser et al.

[11] Patent Number: 5,750,732
[45] Date of Patent: May 12, 1998

[54] METHOD TO PRODUCE CYCLIC ESTERS

[75] Inventors: Dan W. Verser, Golden; Alex Cheung, Fort Collins; Timothy J. Eggeman, Lakewood; William A. Evanko, Golden; Kevin H. Schilling; Manfred Meiser, both of Arvada; Anthony E. Allen, Denver, all of Colo.; Melville E. D. Hillman, Hilliard, Ohio; George E. Cremeans, Groveport, Ohio; Edward S. Lipinsky, Worthington, Ohio

[73] Assignee: Chronopol, Inc., Golden, Colo.

[21] Appl. No.: 444,954

[22] Filed: May 19, 1995

Related U.S. Application Data

[63] Continuation of Ser. No. 128,797, Sep. 29, 1993, Pat. No. 5,420,304, which is a continuation-in-part of Ser. No. 854,559, Mar. 19, 1992, Pat. No. 5,319,107.

[51] Int. Cl.$^6$ .................... C07D 321/00; C07D 321/10
[52] U.S. Cl. .................... 549/274; 549/349; 525/185; 525/437
[58] Field of Search .................... 549/274, 349; 525/185, 437

[56] References Cited

U.S. PATENT DOCUMENTS

| | | | |
|---|---|---|---|
| 1,095,205 | 5/1914 | Gruter et al. | 260/2 |
| 1,594,843 | 8/1926 | Lawrie | 260/2 |
| 1,906,068 | 4/1933 | Jenemann | 260/2 |
| 1,995,970 | 3/1935 | Dorough | 260/2 |
| 2,163,268 | 6/1939 | Carothers et al. | 260/338 |
| 2,174,491 | 9/1939 | Watson | 260/67 |
| 2,189,572 | 2/1940 | Watson | 260/78 |
| 2,668,162 | 2/1954 | Lowe | 260/78.3 |
| 2,703,316 | 3/1955 | Schneider | 260/78.3 |
| 2,758,987 | 8/1956 | Salzberg | 260/78.3 |
| 2,768,973 | 10/1956 | Castle et al. | 260/602 |
| 3,322,719 | 5/1967 | Peilstöcker | 260/45.8 |
| 3,371,112 | 2/1968 | Winstrom et al. | 260/535 |
| 3,435,008 | 3/1969 | Schmitt et al. | 260/78.3 |
| 3,457,280 | 7/1969 | Schmitt et al. | 260/340.2 |
| 3,597,450 | 8/1971 | Schmitt et al. | 260/340.2 |
| 3,736,646 | 6/1973 | Schmitt et al. | 29/458 |
| 3,867,190 | 2/1975 | Schmitt et al. | 117/138.8 |
| 3,960,152 | 6/1976 | Augurt et al. | 128/335.5 |
| 4,033,938 | 7/1977 | Augurt et al. | 260/78.3 |
| 4,045,418 | 8/1977 | Sinclair | 260/78.3 |
| 4,070,375 | 1/1978 | Suzuki | 260/340.6 |
| 4,435,595 | 3/1984 | Agreda et al. | 560/234 |
| 4,650,851 | 3/1987 | Rhum et al. | 528/354 |
| 4,727,163 | 2/1988 | Bellis | 549/274 |
| 4,730,082 | 3/1988 | Amiet | 560/227 |
| 4,771,001 | 9/1988 | Bailey et al. | 435/139 |
| 4,797,468 | 1/1989 | De Vries | 528/354 |
| 4,835,293 | 5/1989 | Bhatia | 549/274 |
| 4,939,294 | 7/1990 | Agreda et al. | 560/265 |
| 4,966,982 | 10/1990 | Ono et al. | 549/274 |
| 4,990,222 | 2/1991 | Aigner et al. | 203/91 |
| 5,023,349 | 6/1991 | Bhatia | 549/274 |
| 5,023,350 | 6/1991 | Bhatia | 549/274 |
| 5,043,458 | 8/1991 | Bhatia | 549/274 |
| 5,053,485 | 10/1991 | Nieuwenhuis et al. | 528/354 |
| 5,053,522 | 10/1991 | Muller | 549/274 |
| 5,068,418 | 11/1991 | Kulprathipanja et al. | 562/580 |
| 5,075,115 | 12/1991 | Brine | 424/486 |
| 5,089,632 | 2/1992 | Paul | 549/274 |
| 5,091,544 | 2/1992 | Bhatia | 549/274 |
| 5,236,560 | 8/1993 | Drysdale | 203/99 |
| 5,264,592 | 11/1993 | Fridman et al. | 549/274 |
| 5,310,599 | 5/1994 | Ford | 528/354 |

FOREIGN PATENT DOCUMENTS

| | | |
|---|---|---|
| 863673 | 2/1971 | Canada . |
| 0 261 572 A1 | 3/1988 | European Pat. Off. . |
| 0 264 926 A2 | 4/1988 | European Pat. Off. . |
| 0 275 581 A1 | 7/1988 | European Pat. Off. . |
| 221786 | 5/1910 | Germany . |
| 267826 | 12/1913 | Germany . |
| 53 074 | 5/1967 | Germany . |
| 36 32 103 A1 | 3/1988 | Germany . |
| 1007347 | 10/1965 | United Kingdom . |
| 1122229 | 7/1968 | United Kingdom . |
| WO 91/17155 | 11/1991 | WIPO . |
| WO 92/00292 | 1/1992 | WIPO . |

OTHER PUBLICATIONS

Jungfleisch et al., "Organic Chemistry—of Lactyllactyllactic Acid and the Dilactide of Racemic Lactic Acid", pp. 502–505, 1905, Academie des Sciences, Meeting of 20 Feb.

Jungfleisch et al., "Organic Chemistry—On the Dilactide of Left Lactic Acid", pp. 637–639, 1906, Academie Des Sciences, Meeting of 12 Mar.

Jungfleisch et al., "Organic Chemistry — On The Dilactide of the Right", pp. 111–113, 1905 Academie des Sciences, Meeting of 10 Jul.

Jungfleisch et al., "Organic Chemistry—On Inactive Dilactylic Acid", p. 979, 1907, Academie des Sciences, Meeting of 6 May.

(List continued on next page.)

*Primary Examiner*—C. Warren Ivy
*Assistant Examiner*—Raymond Covington
*Attorney, Agent, or Firm*—Sheridan Ross P.C.

[57] ABSTRACT

Disclosed is a novel integrated process for production of cyclic esters which includes recovery of starting materials, such as lactic acid from a dilute aqueous lactic acid-containing solution, by solvent extraction. The starting materials are then formed into cyclic esters by removal of water wherein the concentration of higher molecular weight oligomers is maintained below about 20 wt % of the reaction composition. The process further includes providing a recovery solvent for the reaction composition and separating the cyclic esters from the starting materials and higher molecular weight oligomers by liquid-liquid equilibrium separation. The present invention is further directed toward independent novel unit operations of the overall process. The present invention provides for the efficient production and recovery of cyclic esters due to integration of the various unit operations by use of appropriate solvents and recycle streams. In addition, high rates of conversion of starting materials and high rates of selective production of cyclic esters are achieved by appropriate control of process parameters.

16 Claims, 15 Drawing Sheets

OTHER PUBLICATIONS

Jungfleisch et al., "Organic Chemistry—On Ethyl Lactyllactate", 1907, Academie des Sciences, Meeting of 25 Feb.

King, "Amine–Based Systems for Carboxylic Acid Recovery", pp. 285–291, 1992, Chemtech, Mar.

Kleine et al., "High Molecular Weight, Especially Optically Active Polyesters of Lactic Acid: An Investigation of the Stereochemistry of Macromolecular Compounds", pp. 1–21, 1958, Report from the Research Laboratory for Macromolecular Chemistry, Dec.

Kulkarni et al., "Polylactic Acid for Surgical Implants", pp. 839–843, 1966, Arch. Surg., vol. 93, Nov.

Light, "Lactic Acid Resins", pp. 135–136, 1940, Paint Manufacture, Jun.

Marlatt et al., "Acetone–Butanol Fermentation Process Development and Economic Evaluation", pp. 23–28, 1986, Biotechnology Progress, vol. 2, No. 1.

Montgomery, "Acidic Constituents of Lactic Acid–Water Systems", pp. 1466–1468, 1952, J. Am. Chem. Soc., vol. 74.

Othmer, "Acetic Acid Recovery Methods", pp. 48–59, 1958, Chemical Engineering Progress, vol. 54, No. 7.

Ratchford et al., "Extraction of Lactic Acid From Water Solution", pp. 778–781, Industrial and Engineering Chemistry, vol. 43, No. 3.

Ricker et al., "Solvent Extraction for Treatment of Wastewaters from Acetic–Acid Manufacture," p. 204–209, 1978, The American Institute of Chemical Engineers, vol. 74, No. 178.

Tamada et al., "Extraction of Carboxylic Acids with Amine Extractants. 1. Equilibria and Law of Mass Action Modeling", pp. 1319–1326, 1990, Ind. Eng. Chem. Res., vol. 29, No. 7.

Tamada et al., Extraction of Caboxylic Acids with Amine Extractants. 2. Chemical Interactions and Interpretation of Data, pp. 1327–1333, 1990, Ind. Eng. Chem. Res., vol. 29, No. 7.

Tamada et al., "Extraction of Carboxylic Acids with Amine Extractants. 3. Effect of Temperature, Water Coextraction, and Process Considerations", pp. 1333–1338, 1990, Ind. Eng. Chem., Res., vol. 29, No. 7.

Terrill et al., "Separation of Closely Boiling Mixtures by Reactive Distillation 1. Theory", pp. 1062–1071, 1985, Ind. Eng. Chem. Process Des. Dev., vol. 24, No. 4.

Watson, "Composition of Lactic Acid. Production of a Highly Concentrated Acid", pp. 399–401, 1940, Industrial and Engineering Chemistry, vol. 32, No. 3.

Wise, "Biopolymeric Controlled Release Systems", pp. 187–199, 1984, CRC Press, vol. 2.

Wise, et al., "Lactic/Glycolic Acid Poymers", pp. 237–270, Dynatech R/D Company, Cambridge, Mass., U.S.A.

Wise, "Biopolymeric Controlled Release Systems", pp. 3–28, 1984, CRC Press, vol. 1.

Wislicenus, "On the Optically Active Lactic Acid of Sarcolactic Liquid, The Paralactic Acid", pp. 318–319, 1873, Liebigs Ann. Chem. vol. 167.

CA 113 No. 6740, Valle, "Prep. of crosslinks carboxy polysaccharide." 1989.

CA 106 No. 119576, Kharrat, "Intramolecular homolytic amplitudes" 1986.

Alen et al., "Condensation of Glycolic, Lactic and 2–Hydroxybutanoic Acids During Heating and Identification of the Condensation by GLC–MS", pp. 633–636, 1980, Acta Chemica Scandinavica B, vol. 34, No. 9.

Bezzi et al., "Dehydration Products of Lactic Acid Typifying the Transformation of Cyclic Esters into Linear Polyesters", 1936, Meeting of the Italian Academy of Science, Nov.

Bezzi, "The Constitution of Some Polyglycolides", pp. 219–233, 1949, Gazz Chim. Ital. vol. 79.

Bezzi, "Transformation of Cyclic Esters into Linear Polyesters", pp. 215–224, 1938, Gazz. Chim. Ital. vol. 68.

Bischoff et al., "Ueber Das Glycolid Und Seine Homologen", 1893, pp. 262–265, Chem. Ber, vol. 26.

Bureau, "What the Printer Should Know About Paper", pp. 38, 39, 59. Graphic Arts Technical Foundation.

Busche, "Recovering Chemical Products from Dilute Fermentation Broths", pp. 597–615, 1983, Biotechnology and Bioengineering Symp., No. 13.

Carothers, "Polymers and Polyfunctionality", pp. 39–53, 1936, Transactions of the Faraday Society, vol. 32.

Carothers et al., "Studies of Polymerization and Ring Formation. X. The Reversible Polymerization of Six–Membered Cyclic Esters", pp. 761–771, 1932, J. Am. Chem. Soc., vol. 54.

Cleary et al., "Separation of Closely Boiling Mixtures by Reactive Distillation. 2. Experiments", pp. 1071–1073, 1985, Ind. Eng. Chem. Process Des. Dev., vol. 24.

Dadgar et al., "Improving the Acetone–Butanol Fermentation Process with Liquid–Liquid Extraction", pp. 36–39, 1988, Biotechnology Progress, vol. 4, No. 1.

DeGarmo et al., "Consider Reactive Distillation", pp. 43–50, 1992, Chemical Engineering Progress, Mar.

Deibig et al., "I. Synthesis and Properties of Polytetramethyl Glycolide", pp. 123–131, 1971, Die Makromolekulare Chemie, vol. 145.

Deibig et al., "II. Thermal Behavior of Polytetramethyl Glycolide", pp. 133–139, 1971, Die Makromolekulare Chemie, vol. 145.

Earhart et al., "Waste Recovery: Recovery of Organic Pollutants Via Solvent Extraction", pp. 67–73, 1977, CEP, May.

Filachione et al., "Lactic Acid Condensation Polymers: Preparation by Batch and Continuous Methods", pp. 223–228, 1944, Industrial and Engineering Chemistry, March, vol. 36, No. 3.

Hill et al., "Cyclic and Polymeric Formals", pp. 925–928, 1935, J. Am. Chem. Soc., vol. 57.

Holten, "Lactic Acid. Properties and Chemistry of Lactic Acid and Derivatives", pp. 221–231, 1971, Verlag Chemie.

Ikada et al., "Stereocomplex Formation Between Enantiomeric Poly(Lactides)", pp. 904–906, 1987, American Chemical Society, Macromolecules, 20.

Imasaka et al., "Synthesis of Degradable Terpolymers Responding to External Stimuli Such as PH, Ionic Strength, and Temperature", pp. 715–722, 1991, Makromol. Chem. vol. 192.

Jackanicz et al., "Polylactic Acid as a Biodegradable Carrier for Contraceptive Steroids", pp. 227–234, 1973, The Population Counsel, Sep., vol. 8, No. 3.

4 Different Concentrations of Sulfuric Catalyst in Xylene

| Time | conv | select LD | LD Product |
|---|---|---|---|
| 6 | 0.56 | 0.24 | 0.14 |
| 15 | 0.79 | 0.27 | 0.21 |
| 25 | 0.84 | 0.28 | 0.23 |
| 40 | 0.86 | 0.29 | 0.25 |
| 60 | 0.84 | 0.31 | 0.26 |
| 82 | 0.81 | 0.31 | 0.25 |
| 103 | 0.80 | 0.33 | 0.27 |
| 128 | 0.77 | 0.34 | 0.26 |
| 140 | 0.76 | 0.35 | 0.26 |
| 165 | 0.73 | 0.37 | 0.27 |
| 190 | 0.72 | 0.37 | 0.27 |
| 230 | 0.68 | 0.40 | 0.27 |
| 250 | 0.65 | 0.41 | 0.27 |
| 270 | 0.65 | 0.41 | 0.26 |

| Time | convers. | LD Selectivity | LD product |
|---|---|---|---|
| 4 | 0.28 | 0.39 | 0.11 |
| 9 | 0.38 | 0.58 | 0.22 |
| 14 | 0.52 | 0.69 | 0.36 |
| 19 | 0.57 | 0.72 | 0.41 |
| 24 | 0.62 | 0.71 | 0.44 |
| 30 | 0.64 | 0.72 | 0.46 |
| 36 | 0.68 | 0.72 | 0.49 |
| 43 | 0.71 | 0.73 | 0.52 |
| 52 | 0.72 | 0.73 | 0.53 |
| 62 | 0.75 | 0.73 | 0.55 |
| 90 | 0.83 | 0.72 | 0.60 |
| 103 | 0.81 | 0.74 | 0.60 |
| 134 | 0.83 | 0.75 | 0.62 |
| 162 | 0.85 | 0.76 | 0.65 |
| 193 | 0.88 | 0.76 | 0.67 |
| 232 | 0.89 | 0.77 | 0.68 |
| 278 | 0.92 | 0.80 | 0.74 |
| 312 | 0.92 | 0.81 | 0.75 |
| 354 | 0.82 | 0.93 | 0.76 |
| 404 | 0.86 | 0.94 | 0.81 |

METHOD TO PRODUCE CYCLIC ESTERS

CROSS-REFERENCE TO RELATED APPLICATIONS

This is a continuation of application Ser. No. 08/128,797 filed on Sep. 29, 1993, issued as U.S. Pat. No. 5,420,304 on May 30, 1995 which is a continuation-in-part of U.S. Patent application Ser. No. 07/854,559, filed Mar. 19, 1992, now U.S. Pat. No. 5,319,107 the disclosure of which is incorporated herein by reference in its entirety.

FIELD OF THE INVENTION

The present invention relates to a method for the manufacture of cyclic esters by the conversion of hydroxycarboxylic acids (referred to herein as hydroxy acids or hydroxycarboxylic acids) and their derivatives to their respective cyclic esters, preferably cyclic compounds with two esters in the same ring. The invention also includes novel techniques for the recovery of hydroxy acids to form a feedstream and for recovery of cyclic esters.

BACKGROUND OF THE INVENTION

Cyclic esters, including cyclic esters of the general formula

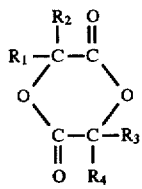

wherein $R_1$, $R_2$, $R_3$, and $R_4$ can be either hydrogen or substituted or unsubstituted aliphatic or aryl hydrocarbon having from 1 to about 10 carbon atoms, are a useful class of compounds that can be polymerized into polymeric materials. Such polymeric materials are particularly useful in the preparation of environmentally biodegradable plastic materials and of plastic materials which resorb when used in medical applications. Polymers made from the polymerization of cyclic esters such as lactide are particularly useful because they can be degraded over time by water hydrolysis under most environmental conditions. The resulting hydroxy acid units (e.g., lactic acid) or oligomers thereof are then readily taken up by microorganisms in the environment and converted to carbon dioxide and water aerobically or carbon dioxide and methane anaerobically. Cyclic esters are also useful as plasticizers and intermediates for production of surface-active agents and plasticizers.

In accordance with prior practice, the desired cyclic esters were prepared by first condensing hydroxy acids, typically a-hydroxy acids, to an oligomeric prepolymer of relatively high molecular weight. The prepolymer was then depolymerized at high temperature and low pressure in a heated, evacuated reactor to a crude cyclic ester. Extensive purification processes were required to obtain cyclic esters of requisite purity to be sufficient to synthesize polymers of desired molecular weight.

The production of a cyclic ester from an oligomeric α-hydroxy acid prepolymer is sometimes referred to as a back-biting reaction since it involves the step-wise removal of cyclic dimer esters from the tail ends of the prepolymer to form the cyclic ester as illustrated below with reference to a lactic acid oligomer.

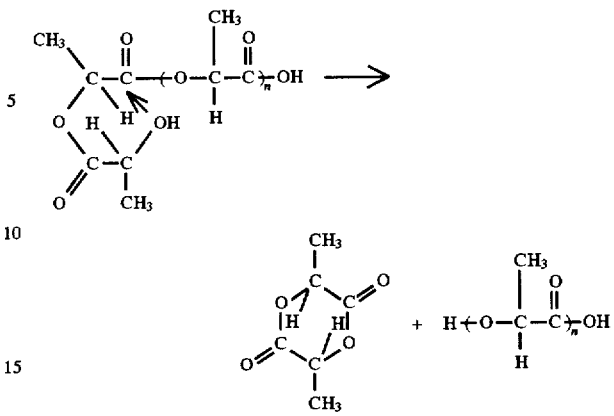

U.S. Pat. No. 4,727,163 to Bellis is directed to a process which includes first making a prepolymer comprising a block polymer that includes a thermally stable polyether core with an α-hydroxy acid or its ester polymerized onto the core. Upon heating under vacuum conditions, the chain ends of the α-hydroxy acids are thermally degraded to form a cyclic ester which can be condensed under vacuum.

U.S. Pat. No. 4,835,293 to Bhatia is directed to a back-biting process which includes the use of an inert gas sweep which permits the process to be operated at or above atmospheric pressure. The inert gas intimately contacts the prepolymer, which is in the liquid phase, so as to create a large interfacial area between the prepolymer and the inert gas to vaporize the cyclic ester and sweep the vapors out of the reactor for subsequent recovery and purification.

As illustrated above, and as discussed in the referenced Bellis and Bhatia patents, back-biting depolymerization of an α-hydroxy acid can result in the production of a cyclic ester. However, the back-biting reaction is typically a slow one, and is conducted as a batch operation which extends over significant time and which results in an undesirable high molecular weight byproduct heel which must be disposed of; moreover, the cyclic ester product must be separated from noxious discolored pyrolysis products.

SUMMARY OF THE INVENTION

The present invention is directed toward a process for producing cyclic esters, such as lactide. In one embodiment, the present invention is directed toward an integrated process which includes recovery of starting materials for the production of cyclic esters, formation of cyclic esters and recovery of cyclic esters. In one such process, an XA-containing aqueous solution, such as a dilute lactic acid solution, is contacted with an extraction solvent to form a first phase comprising the extraction solvent, XA and water and a second phase comprising a raffinate. The first phase is then contacted with a cyclic ester production solvent to form a reaction composition. The production solvent has a boiling point higher than the boiling point of the extraction solvent and higher than the boiling point of water. The process further involves selectively removing the extraction solvent from the reaction composition and selectively removing water from the reaction composition to form cyclic esters. The cyclic esters are formed wherein the concentration $X_5A$ and higher oligomers is less than about 20 wt % of the reaction composition. The process further includes providing a recovery solvent for the reaction composition and separating the cyclic esters and recovery solvent from $X_1A$ and oligomers of $X_1A$ by a liquid-liquid equilibrium separation. The cyclic esters are then recovered from the recovery solvent.

Further embodiments of the invention are directed toward various independent unit operations of the overall integrated process. In particular, one embodiment of the present invention includes a process for producing an XA-containing feedstream capable of being used in cyclic ester production. This process includes extracting XA from an XA-containing aqueous solution with a first solvent having a distribution coefficient for said XA with respect to water of at least about 0.2 to form a first phase comprising said first solvent and XA and a second phase comprising a raffinate. The process further includes contacting the first phase with a second solvent to form the XA-containing feedstream, wherein the second solvent has a boiling point higher than the boiling point of the first solvent and higher than the boiling point of water.

In a further embodiment, the present invention includes a process for producing cyclic esters which includes providing a feedstream comprising XA in a solvent and removing water from the feedstream and forming cyclic esters, wherein the concentration of $X_5A$ and higher oligomers formed from the feedstream is less than about 20 wt% of the reaction mixture during process. In another embodiment, the process is conducted by maintaining the water concentration in the feedstream below about 2 wt %. In another embodiment, XA comprises $X_1A$ and $X_1A$ is selected from the acids, esters, salts or amides of the group consisting of lactic acid, glycolic acid, tartaric acid, mandelic acid, 1-hydroxy 1-cyclohexane carboxylic acid, 2-hydroxy-2-(2-tetrahydrofuranyl) ethanoic acid, 2-hydroxy-2-(2-furanyl) ethanoic acid, 2-hydroxy-2-phenylpropionic acid, 2-hydroxy-2-methylpropionic acid, 2-hydroxy-2-methylbutanoic acid, 2-hydroxybutanoic acid, 2-hydroxypentanoic acid, and mixtures thereof.

In a further embodiment, the invention includes a process to produce cyclic esters with high rates of conversion of reactants into products. This embodiment includes providing a feedstream comprising XA in a solvent and removing water from the feedstream to form cyclic esters, wherein the concentration of $X_5A$ and higher oligomers is less than about 20 wt % of the reaction mixture during the process and wherein the conversion of the process is at least about 30%. In one embodiment, high conversion rates are achieved by use of a feedstream having an XA concentration of at least about 5 wt %. This embodiment can further include maintaining the reaction temperature above about 110° C. In addition, high conversion rates can be achieved by use of an esterification catalyst.

In a further embodiment of the present invention, cyclic esters are produced with a high degree of selectivity, in which a high proportion of XA components which are converted are converted selectively to XD species rather than higher oligomeric linear species of XA. In one embodiment, this process includes providing a feedstream comprising XA in a production solvent and removing water from the feedstream to form cyclic esters, wherein the concentration of $X_5A$ and higher oligomers is less than about 20 wt % of the reaction mixture during the process and wherein the selectivity of the process is greater than about 30%. In one embodiment, the production solvent is selected from the group consisting of toluene, xylene, anisole, phenetole, 4-methyl anisole, 1,3-dimethoxy benzene, mesitylene and mixtures thereof. In a further embodiment, the production solvent comprises an aromatic solvent selected from the group consisting of monosubstituted and disubstituted solvents. In a further embodiment, the production solvent can include a mixed solvent comprising first and second solvents having different polarities. The production solvent and $X_1A$ can have polar or H-bonding solubility parameter components within about 10 $MPa^{1/2}$ of each other. Further, the production solvent can have a dipole moment of greater than about 0.5 Debye.

The process for producing cyclic esters can be conducted using a variety of process configurations. The process can be batch, fed-batch or continuous. In one embodiment, a continuous process can be conducted sequentially in at least a first and second reaction vessel. In another embodiment, the first reaction vessel can be a water stripping column. In another embodiment, the reaction may be carried out entirely in a distillation column. In a further embodiment, the process can have a volumetric efficiency of at least about 10 g of cyclic ester per liter per hour.

A further embodiment of the present invention is a process for the recovery of cyclic ester from a cyclic ester production mixture which includes cyclic esters, $X_1A$ and oligomers of $X_1A$. This embodiment includes providing a recovery solvent for the cyclic ester production mixture and separating at least a portion of the cyclic esters and recovery solvent from $X_1A$ and oligomers of $X_1A$ by liquid-liquid equilibrium separation. The process further includes recovering cyclic esters from the cyclic ester and recovery solvent. In one embodiment, the cyclic ester has a separation factor with respect to $X_1A$ in the recovery solvent at about room temperature at 1 atm of at least about 1. The recovery solvent can be selected from the group consisting of xylene, toluene, benzene, methyl isobutyl ketone (MIBK), isopropyl ether and mixtures thereof. In a further embodiment, the step of recovering comprises a process selected from the group consisting of distillation, solvent crystallization, melt crystallization and mixtures thereof.

A further embodiment of the present invention is for the purification of cyclic ester from a cyclic ester mixture which includes cyclic ester, $X_1A$, oligomers of $X_1A$ and solvent which includes selectively distilling at least a portion of $X_1A$ and solvent from the cyclic ester mixture; selectively distilling at least a portion of cyclic ester from the mixture; and subsequently recovering the distilled cyclic ester.

A further embodiment of the present invention is for the purification of cyclic ester from a cyclic ester mixture which includes cyclic esters, $X_1A$ and oligomers of $X_1A$. The process includes heating the cyclic ester mixture to above the melting point of the cyclic ester and maintaining the mixture at a temperature between the melting point of the cyclic esters and about 20° C. less than the melting point of the cyclic ester to allow crystal formation and recovering the crystallized cyclic esters.

DETAILED DESCRIPTION

Figure 1:
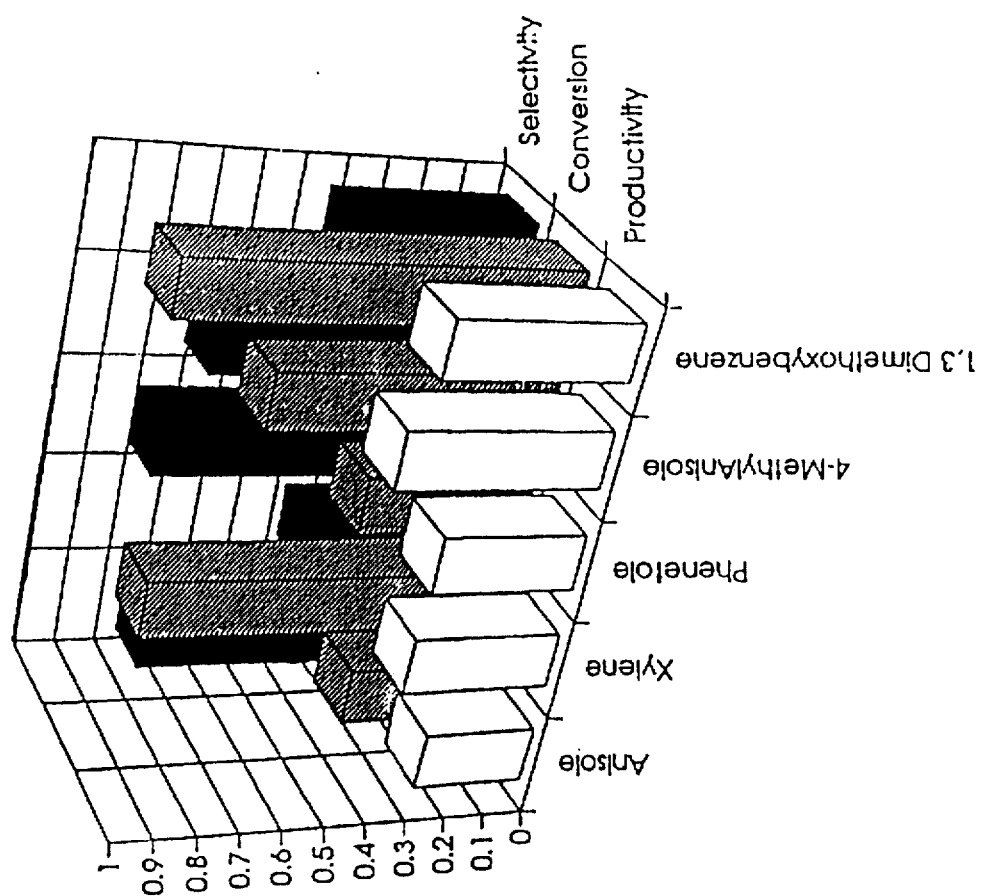
FIG. 1 is a three-dimensional representation of selectivity, conversion and productivity in the production of lactide using different production solvents.

The present invention provides an integrated process for the production of cyclic esters, such as lactide. The process includes the recovery of starting materials, such as lactic acid; production of cyclic esters from the starting materials; and recovery of cyclic esters. The process is particularly beneficial because the various unit operations are integrated by use of solvents and/or catalysts which are advantageous in multiple unit operations. Therefore, the product stream from one unit operation can be used as the feedstream for a subsequent unit operation. Thus, the process or segments of the process can be conducted as continuous operations. Moreover, the process includes a number of recycle streams between the various unit operations. The process provides an efficient method for the production of cyclic esters. In addition, many aspects of the process are novel and useful independent of the overall process.

CHEMISTRY OF CYCLIC ESTER PRODUCTION

The present invention provides a process to produce cyclic esters derived from hydroxycarboxylic acids, hydroxycarboxylic acid esters, hydroxycarboxylic acid salts, or hydroxycarboxylic acid amides. As used herein, the term "derived from" refers to the cyclic ester being produced by reactions in which these components or products of these components are reactants. Preferably, the cyclic esters are formed by converting an ester formed from any two hydroxy acids, esters, salts, or amides thereof, into a cyclic ester. Such preferred cyclic esters are referred to herein as XD. As used herein, $X_1A$ refers to a hydroxycarboxylic acid, hydroxycarboxylic acid ester, hydroxycarboxylic acid salt, or hydroxycarboxylic acid amide. $X_2A$ refers to a linear dimer molecule of a hydroxy acid or its derivative. $X_3A$ refers to a linear trimer molecule of a hydroxy acid or its derivative, and $X_nA$ refers to a linear n-mer molecule of a hydroxy acid or its derivative. As used herein, XA without subscript denotes one or more of $X_1A$, $X_2A$, $X_3A$, and $X_4A$ or a solution containing those species. It will be understood that when X is substituted by L, G or T, the corresponding compounds based on lactic, glycolic and tartaric acid, respectively, are meant. For example, LA refers to a lactic acid-based mixture, including $L_1A$, $L_2A$, $L_3A$ and $L_4A$, and LD refers to lactide.

In accordance with an embodiment of the present invention, a cyclic ester derived from $X_1A$ is produced by providing a feedstream containing components including, but not limited to, XA and treating the feedstream to form the cyclic ester. While not wishing to be bound by theory, it is believed that the cyclic ester is formed primarily directly from $X_2A$. Under certain reaction conditions, it is believed that $X_3A$ and $X_4A$ may contribute to cyclic ester formation in a minor amount. However, this mechanism is not essential to the current invention. As used herein, forming the cyclic ester primarily directly from $X_2A$ refers to a reaction in which $X_2A$ already present in the feedstream or $X_2A$ formed by an esterification reaction between two $X_1A$ molecules is converted to a cyclic ester by esterification. That is, it appears that the cyclic ester is not formed by backbiting of polyester chains, as described in the prior art when a cyclic ester is formed from $X_5A$ or greater.

The process of the present invention and that described in related application U.S. Ser. No. 07/854,559 is novel and distinguishable from the previously known processes of depolymerization of higher oligomers because it is believed that the present process forms XD molecules directly from $X_2A$ molecules by cyclization thereof. It should be noted that reaction conditions for the present process are significantly milder than for known depolymerization reactions. For example, depolymerization reactions are typically conducted at temperatures of above about 200° C. Because XD is believed to be formed directly from $X_2A$, substantial amounts of higher oligomeric species such as $X_5A$ and higher oligomers are not formed from XA species, as is required in the pre-polymers used in the traditional depolymerization process to yield XD. Thus, a unique aspect of the present invention is the reaction of the feedstream of the present invention under conditions such that the total concentration of $X_5A$ and higher oligomers in the reaction mixture formed from XA in the feedstream remains below about 20 wt % of the reaction mixture, more preferably less than about 15 wt %, and most preferably less than about 10 wt %.

According to the present invention, $X_1A$ is preferably an α-hydroxycarboxylic acid, or an ester, salt, or amide thereof. While not wishing to be bound by theory, it is believed that α-hydroxycarboxylic acids or derivatives thereof are particularly suitable for forming XD cyclic esters. A wide variety of α-hydroxycarboxylic acids and their derivatives may be converted to cyclic esters in accordance with the present invention. Such acids include acids of the formula $R_1R_2C(OH)-COOH$ wherein $R_1$ and $R_2$ are each independently hydrogen or substituted or unsubstituted aliphatic or aryl hydrocarbons having 1 to 10 carbon atoms and the water soluble esters, salts or amides of such acids. A single $X_1A$ or mixtures of different $X_1A$ species may be used. Suitable $X_1A$ compounds include, but are not limited to, the following acids and corresponding esters, salts, or amides thereof: lactic acid ($L_1A$), glycolic acid ($G_1A$), tartaric acid ($T_1A$), mandelic acid, malic acid, 1-hydroxy 1-cyclohexane carboxylic acid, 2-hydroxy-2-(2-tetrahydrofuranyl) ethanoic acid, 2-hydroxy-2-(2-furanyl) ethanoic acid, 2-hydroxy-2-phenylpropionic acid, 2-hydroxy-2-methylpropionic acid, 2-hydroxy-2-methylbutanoic acid, 2-hydroxybutanoic acid, 2-hydroxypentanoic acid, and mixtures thereof.

Preferred acids are lactic, glycolic and tartaric acids, with lactic acid being more preferred. Preferred salts are alkyl or aryl amine salts of XA, more preferably ammonium salts of XA, such as ammonium lactate or alkyl ammonium lactates. Additional preferred salts include other lactate, glycolate, and tartrate salts. Suitable esters include short chain alkyl esters, such as those with methyl, ethyl, or butyl chains, as well as those with longer chains, such as octadecyl lactate. Preferred esters include methyl lactate, ethyl lactate and octadecyl lactate. Reference to esters of $X_1A$ does not refer to oligomeric esters or polyesters of $X_1A$. $X_1A$ can be either stereoisomer, namely L- or D-.

Preferred $X_2A$ components are esters between any two hydroxy acids, salts, esters, amides, or mixtures thereof, including $L_1A$-$L_1A$ (or $L_2A$, also known as lactoyllactic acid or lactic acid dimer), $L_1A$-$G_1A$, $L_1A$-$T_1A$, $G_1A$-$G_1A$ (or $G_2A$), $G_1A$-$T_1A$, and $T_1A$-$T_1A$ (or $T_2A$) esters. For example, $L_2A$ can be represented as follows:

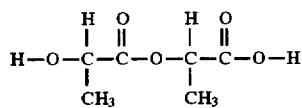

Preferred $X_2A$ components are $L_2A$, $L_1A$-$G_1A$, and $G_2A$ esters. $X_2A$ can contain two L- isomers, two D- isomers or both a D- and an L- isomer. Furthermore, preferred $X_2A$ type esters are methyl lactoyllactate, ethyl lactoyllactate, butyl lactoyllactate, octadecyl lactoyllactate, and ammonium lactoyllactate.

The process of the present invention is particularly useful when $X_1A$ is a relatively high molecular weight species because production of cyclic esters from such $X_1A$ molecules by conventional backbiting methods is difficult or impossible since isolation of the cyclic ester product is typically accomplished by vaporization of the ester. High molecular weight esters would tend to degrade rather than vaporize. In the present invention, recovery of the product does not require vaporization. For example, such high molecular weight $X_1A$ species include but are not limited to hydroxyisobutyric acid, α-hydroxyisovaleric acid, α-hydroxycaproic acid, α-hydroxyisocaproic acid, and α-hydroxyoctanoic acid.

The role played by water in the present process can be appreciated by reference to the following equilibrium reactions:

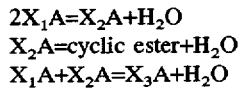

Thus, it will be observed that $X_1A$ is in equilibrium with higher oligomers of $X_1A$, cyclic esters and water. By removing water, the reactions are driven to the right and, conversely, by adding water the reactions are driven to the left.

An important aspect of the present invention is the control of a number of process parameters to favor the desired reaction products. To more precisely understand the use of these parameters, the following defined terms are useful.

The term "conversion" refers to the percentage of $X_1A$ and $X_2A$ (calculated as $X_1A$ equivalents) which is reacted to form either XD or XA oligomers. Thus, for example, if a feedstream initially has 100 units of $X_1A$ and $X_2A$ (expressed on an $X_1A$ basis) and 60 units react to form 30 XD molecules, 30 units react to form $X_3A$ or larger oligomers, and the remaining 10 units of $X_1A$ and $X_2A$ remain unreacted, the conversion is calculated to be 90%.

The term "selectivity" refers to the percentage of converted feedstream which is formed into XD molecules rather than $X_3A$ or larger oligomers. Thus, in the above example, the converted feedstream was 90% of the initial feedstream and, of that 90%, 67% (60%/90%) was selectively converted to XD rather than $X_3A$ or larger oligomers. It is important to note that the use of these terms assumes that the reaction is taking place under non-depolymerization conditions (i.e., non-backbiting). Thus, XD is formed directly from $X_2A$ species, rather than from depolymerization of higher oligomers.

"Productivity" of a reaction, as used herein, refers to the product of the conversion for the reaction multiplied by the selectivity of the reaction. Thus, in the above example, the conversion rate is 90% and the selectivity is 67%. Thus, the overall productivity is 60.0%.

FEEDSTREAMS FOR CYCLIC ESTER PRODUCTION

The feedstream of the present process can contain components in addition to XA, including small amounts of oligomers of $X_1A$, such as $X_5A$ or $X_6A$, and other materials. Preferably, XA components constitute at least about 70 wt %, more preferably 85 wt % and more preferably 90 wt % of total $X_nA$ species. For example, commercial lactic acid is a suitable feedstream and it typically contains from about 70 wt % to about 81 wt % $L_1A$, from about 17 wt % to about 23 wt % $L_2A$, from about 3 wt % to about 7 wt % $L_3A$, from about 0.6 wt % to about 2 wt % $L_4A$ on a water-free basis.

Feedstream Purity

The feedstream can alternatively contain a substantial amount of impurities, such as a partially purified fermentation broth from a fermentation reaction which contains XA. For example, lactic acid or lactate salts, such as ammonium lactate, can be reacted directly from a fermentation broth to produce XD. The production of XD from ammonium lactate has the added advantage in that the byproducts of the reaction are water and ammonia gas, which can be easily separated from the product stream and recycled.

The feedstream may alternatively contain purified components, such as high purity $L_1A$ or high purity $L_{A2}$. The concentration of reactive components in the feedstream can be adjusted to achieve high productivity of cyclic esters for a given cyclic ester production process such as are described below. As used herein, the term reactive components refers to $X_nA$ components where $n \leq 4$ and preferably to $X_1A$ and $X_2A$ components.

The feedstream can alternatively include heat stable components, such as heat stable LA. As used herein, the term heat stable LA refers to a lactic acid mixture which can include various LA species, but from which impurities that can cause coloration upon heating have been removed.

Recycled Feedstreams

In a preferred embodiment of the present invention, the feedstream can contain reactive components which are derived from recycling of polymeric or oligomeric material wherein the material is made from, for example, cyclic esters made in accordance with this invention. For example, in the case of a cyclic ester such as lactide, polymeric or oligomeric lactic acid can be..produced during lactide production. Such polymeric or oligomeric lactic acid can be recycled by hydrolyzing such materials into lactic acid. Such a hydrolysis product is suitable for use herein in a feedstream.

Preparation of Cyclic Ester Reaction Mixtures From Low Concentration Aqueous Feedstreams In accordance with one embodiment of the present invention, a feedstream of the present invention includes an XA-containing feedstream (i.e., a feedstream containing at least one hydroxycarboxylic acid, ester thereof, salt thereof, and/or amide thereof) prepared in accordance with the following preferred XA-containing feedstream production process of the present invention. This process includes contacting an XA-containing aqueous solution with a first extraction solvent to form a first phase containing XA in the first extraction solvent (i.e., an "XA-containing first extraction solution") and a second phase containing the solution from which the XA was extracted (i.e., a "raffinate"). Depending on the characteristics of the first extraction solvent, the XA-containing first extraction solution can be treated in a variety of ways to prepare an XA-containing feedstream for cyclic ester production. Such embodiments will be disclosed below.

The ability to extract XA into the first extraction solvent depends on several factors, including XA concentration, solubility of XA in the first extraction solvent compared to its solubility in water, solubility of water in the first extraction solvent, ability to separate the XA-containing first extraction solution from the raffinate, temperature, pH, and solvent ratios.

One advantage of using the solvent extraction process of the present invention to prepare XA for cyclic ester production is that the XA need not be concentrated in order to conduct the preferred XA-containing feedstream production process of the present invention. Furthermore, since dilute XA-containing feedstreams are advantageous in the cyclic ester production process of the present invention, use of this preferred XA-containing feedstream production process permits integrated XA and XD production processes that are amenable to continuous production and recycling of solvents without the need to concentrate XA-containing solutions. As such, although the preferred XA-containing feedstream production process can be conducted on an XA-containing aqueous solution comprising any concentration of XA, the process is particularly advantageous for aqueous solutions containing dilute amounts of XA, such as XA-containing recycle streams from a cyclic ester production process (such as that of the present invention) or fermentation broths containing microbially-produced XA. Such fermentation broths often contain salts of the hydroxy acid. Such hydroxy acid salt-containing broths can be acidified prior to extraction or can be submitted directly to extraction. Preferably cells have been removed from such fermentation broths prior to extraction. Additional suitable XA-containing aqueous streams include, but are not limited to, XA-containing byproduct streams, XA-containing waste streams, and XA-containing streams in which XA was produced by, for example, hydrolysis of XA-containing polymers. XA-containing aqueous solutions preferably comprise less than about 50 wt/vol % XA, more preferably less than about 12 wt/vol % XA, and even more preferably less than about 5 wt/vol % XA.

Preferred first extraction solvents are those that have a distribution coefficient (Y) for XA into the solvent with respect to water of at least about 0.2, preferably of at least about 0.5, and more preferably of at least about 1.0. Preferred first extraction solvents can be either essentially insoluble with water or can be partially soluble with water to the extent that, upon extraction, the XA-containing first extraction solution can form a separate phase from the raffinate, thereby providing a simple method for separating the first extraction solution from the raffinate. The determination of the phase equilibria for such systems is well known to those skilled in the art. If a relatively polar solvent is used to extract XA, the formation of two separate phases between that solvent and the aqueous solution may be improved by adding a less polar solvent to the extraction mixture, such as adding xylene to methyl ethyl ketone, thereby forming a mixed solvent.

A preferred embodiment of the present invention is the use of a first extraction solvent that enables the integration of the XA-feedstream production process with the cyclic ester production process in a manner that reduces process steps and cost. Such a first extraction solvent is one that has a boiling point that enables the solvent to be selectively removed by vaporization during the cyclic ester production process; that is, a preferred first extraction solvent has a boiling point lower than the production solvent in which cyclic ester is produced. Any water present in the XA-containing first extraction solution can also be vaporized during cyclic ester production. Alternatively, the first extraction solvent can comprise the cyclic ester production solvent if the cyclic ester production solvent has the appropriate aforementioned characteristics for extracting XA from the XA-containing aqueous solution.

Suitable first extraction solvents of the present invention include organic and silicon-based solvents having the aforementioned characteristics. One class of preferred first extraction solvents includes solvents that are substantially insoluble in water, preferably having a solubility in water of less than about 3 wt/vol %, and more preferably of less than about 0.5 wt/vol %, yet that have an acceptable $K_D$ for XA into the solvent with respect to water. Suitable examples of such solvents include 1-butanol, 2-butanol, ethyl acetate, butyl acetate, methylene chloride, and ethylene chloride. An advantage of such solvents is that, after extraction, the raffinate contains very little of the extraction solvent, thereby reducing the expense required to recover solvent for recycling back into the extraction process. For use in cyclic ester production, the XA-containing first extraction solution can be mixed with the desired cyclic ester production solvent to form the feedstream for cyclic ester formation. Such a feedstream can be submitted to the cyclic ester production process of the present invention, during which the first extraction solvent is vaporized and can be recycled to the extraction process.

A second class of preferred first extraction solvents include solvents that are somewhat soluble in water and, due to their polarity, have desirable $K_D$ for XA into the solvent with respect to water. Suitable solvents of this class include 2-butanone (methyl ethyl ketone or MEK) isopropyl ether, and methyl isobutyl ketone (MIBK). For example, MEK has a $K_D$ for lactic acid with respect to water of about 0.81, a boiling point of about 79.6° C. at atmospheric pressure, and a solubility in water of about 25%. However, due to its partial solubility in water, a substantial proportion of a solvent of this class is retained in the raffinate. In accordance with the present invention, such a limitation can be overcome by performing a second extraction step in which a second extraction solvent is contacted with the raffinate in order to extract a substantial portion of the first extraction solvent into the second extraction solvent, thereby forming a second extraction solution. In accordance with the present invention, the second extraction solvent is preferably the cyclic ester production solvent, such as xylene. Additional suitable and preferred production solvents are disclosed below. A preferred source of the second extraction solvent is a recycle stream recovered from the cyclic ester recovery process, as disclosed below. In this embodiment, the first and second extraction solutions are combined and submitted to the cyclic ester production process of the present invention. During cyclic ester production, both the first extraction solvent and any water present are vaporized and can be recycled to the XA extraction process. In an alternative embodiment, the limitation of having a substantial portion of the first extraction solvent being left in the raffinate can be overcome by combining the first and second extraction solvents in a single extraction step as a mixed solvent. If desired, the resultant XA-containing extraction solution can then be submitted to cyclic ester production processes and the extraction solvents recovered and recycled as disclosed herein.

Another embodiment of the solvent extraction process of the present invention is the use of a first extraction solvent that includes a diluent solvent and an amine, such as a tri-alkyl amine, to improve the $K_D$ for XA into the first extraction solvent with respect to water. The addition of tri-alkyl amines has been shown previously to improve the $K_D$ of an appropriate solvent for a hydroxy acid with respect to water; see for example, U.S. Pat. No. 4,698,303, by Bailey et al., issued Oct. 6, 1987; U.S. Pat. No. 4,771,001, by Bailey et al., issued Sep. 13, 1988; and review by King, May 1992, Chemtech, pp. 285-291. Preferred tri-alkyl amines of the present invention are tri-alkyl amines that are volatile in the cyclic ester production process of the present invention. Suitable tri-alkyl amines include tri-ethyl amine (TEA), and tri-methyl amine (TMA), with TEA being preferred. Suitable solvents in which to dilute the tri-alkyl amines to form the first extraction solvent are diluents that are sufficiently polar to extract the complex formed between TEA and the hydroxy acid salt from water. Such solvents include MEK, MIBK, and methylene chloride, with MEK being preferred. For example, MEK containing TEA has a $K_D$ for lactic acid with respect to water of at least about 2.0. The optimization of the extraction of XA using amines can be determined by those skilled in the art. Either during or after extraction, the first extraction solution can be contacted with a cyclic ester production solvent and submitted to cyclic ester production, during which the first extraction solvent including the tri-alkyl amine, is volatilized and can be recycled to the XA extraction process. During cyclic ester production, volatilization of the tri-alkyl amine converts the hydroxy acid salt into the respective hydroxy acid. Alternatively, the first extraction solvent can comprise a tri-alkyl amine diluted in an appropriate cyclic ester production solvent, such as anisole, xylene, or toluene, in which case the resultant first extraction solution can be submitted directly to the cyclic ester production process.

The extraction processes disclosed herein can be conducted using conventional techniques including, but not limited to, continuous multi-stage extraction processes. Any number of stages necessary to achieve substantial extraction of either the XA or first extraction solvent, as appropriate, can be used in the extraction process.

It should be noted that XA-containing feedstreams prepared according to the preferred process of the present invention can be used not only in cyclic ester production but in any suitable process in which a hydroxycarboxylic acid is a feedstock, including, but not limited to production of oligomers or polymers by direct condensation or esterification reactions.

Introduction of XA-Containing Feedstreams into Cyclic Ester Production Process

Another embodiment of the present invention is the introduction of XA feed materials to a cyclic ester production unit. The XA-containing feedstreams from the previously outlined section can be fed to a cyclic ester production unit so that proper conditions are met that optimize the production of cyclic esters and minimize the production of the oligomers of XA. As discussed elsewhere, concentrations of the reacting species affect the conversion and selectivity achieved in cyclic ester production. XA feed concentration in the reactor can be controlled and conversion and selectivity can be optimized. Examples of the feed conditions which can be manipulated to optimize the reaction are XA feed concentration, solvent selection, and temperature. The factors are controlled to allow for the formation of a homogeneous reaction mixture before the mixture is fed to the cyclic ester production process or just following introduction to the process. A homogeneous reaction mixture of XA and solvent can be achieved in various ways. In one embodiment, the materials are preheated before they are introduced into the cyclic ester production unit. The feedstream, which can consist of the XA and the solvent is heated to a temperature where the XA species are soluble in the solvent.

REACTION MECHANISMS AND CONDITIONS FOR THE PRODUCTION OF CYCLIC ESTERS

A unique and novel aspect of the present invention is the ability to optimize the production of cyclic esters through the control of reaction mechanisms and conditions. As the system inherently involves competing reactions and frequently, in practice, reaction mixtures may include impurities from upstream processes and/or various oligomeric and other components from recycled streams, the integration and control of reaction conditions yields improved processes which generate increased productivities and volumetric efficiencies beyond what may have been expected. Important reaction control aspects of the present invention include solvent selection, temperature, pressure, feed concentration, catalyst selection and concentration, and reaction time.

Water Removal Effects on Cyclic Ester Production

In accordance with the present invention, the feedstream which includes XA, is treated to form cyclic esters. Treatment typically includes water removal from the feedstream to promote production of cyclic esters. Without wishing to be bound by theory, it is believed that the removed water can be derived from at least three sources: (1) free water initially in the feedstream; (2) water derived from an esterification reaction to form a linear ester ($X_nA$, in which n is at least 2) from two XA molecules; and (3) water derived from an esterification reaction to form a cyclic ester from $X_2A$. The feedstream typically has free water which is usually removed first. When the feedstream is thus substantially dehydrated, the esterification of $X_1A$ to $X_2A$ is then favored, which results in the production of additional water. As that water is substantially removed, the esterification of $X_2A$ to a cyclic ester is then favored. It should be noted that the phases of water removal in this process which are described here as being sequential can occur simultaneously. Since free water is removed during treatment, the initial concentration of water in the feedstream need not be limited. Typically, the amount of free water initially in the feedstream is less than about 50 wt/vol % and more preferably is less than about 30 wt/vol %.

Preferably, free water in the feedstream is removed rapidly leading to an essentially dehydrated feedstream having a water concentration of less than about 2 wt %. Water formed by the esterification reactions is preferably removed essentially as fast as it is formed. In particular, water is typically removed at a rate such that the concentration of water in the treated feedstream is less than about 2 wt %, more preferably less than about 1 wt %, and even more preferably less than about 0.5 wt %.

Water can be removed from a liquid phase feedstream by a variety of methods, including, but not limited to: evaporation, a solvent-based reaction process, such as a reactive distillation process (discussed in more detail below), removal of water as an azeotrope from a feedstream in which the reactive components are diluted in a solvent which forms an azeotrope with water, adding a water-getter which preferentially reacts with water, using molecular sieves or partitioning (e.g., osmotic) membranes, using anhydrous salts that form hydrated crystals with water, contacting the feedstream with water absorptive materials, such as polysaccharides (e.g., Ficoll) or silica.

Effect of Solvents on Cyclic Ester Production

A preferred feedstream in the present invention includes XA and a solvent. The solvent has a variety of functions, dependent on the application, including (i) determining the maximum reaction temperature at a given pressure; (ii) removing water from the reaction; (iii) diluting $X_1A$ to enhance selectivity; (iv) acting as a reactant carrier to dissolve reactant species; and preferably, (v) separating XD from oligomers formed during the reaction.

Solvents for use in the present invention are preferably selected such that XA and any water initially present in the feedstream are soluble in the solvent at the desired reaction temperature, concentration of XA and pressure. If XA and/or water are only partially soluble at reaction temperatures, concentrations and pressures, the portion of XA which is not soluble can separate with water in an XA-containing phase, which would have a very high concentration of XA. Such high concentration of XA will tend to promote oligomer formation, rather than the desired formation of XD directly from $X_2A$. In addition, formation of such an XA-containing phase is likely to result in segregation of many catalysts to the XA-containing phase. In preferred embodiments, the solvent is selected such that XA is 100% soluble at reaction temperatures, concentrations and pressures.

An important aspect of the present invention is the selection of solvents which achieve high selectivity in the production of cyclic esters. Without intending to be bound by theory, it is believed that more polar solvents favor the production of $X_2A$ or XD over the production of higher oligomers of XA, thus leading to greater selectivity. It should be noted, however, that conversion can decrease with more polar solvents. More polar solvents can be more reactive with catalysts than less polar solvents. Such reaction will reduce the catalytic capacity of the XD production reaction. For example, a sulfuric acid catalyst is relatively reactive with a solvent such as anisole.

One measure of the polarity of a solvent is the solubility parameter. Solubility parameters can be determined by direct measurement, correlations with other physical parameters, or indirect calculations. The solubility parameters of solvents usually can be determined directly. The solubility parameter has been defined as the square root of the cohesive energy density and describes the attractive strength between molecules of the material. The units used in the following discussion are in $MPa^{1/2}$. Since $X_DA$ species are often relatively polar, such as lactic acid, preferred polar solvents are typically miscible with XA. Complete miscibility of solvents and XA components is expected to occur if the solubility parameters are similar and the degree of hydrogen bonding is similar between the components.

The composite, or Hildebrand, solubility parameter provides another measure of solvent polarity. It is broken into several terms, representing different contributions to the energy of mixing. These components are dispersive, polar and H-bonding. Good solubility is more likely when the composite values of the solvent and solute are within 10 $MPa^{1/2}$ and preferably 5 $MPa^{1/2}$ units of each other. In particular, solubility is better when the polar or the H-bonding terms are within 10 $MPa^{1/2}$ and preferably 5 $MPa^{1/2}$ of each other. Most preferably, solubility is more likely when the polar and the H-bonding terms are within 10 and preferably 5 $MPa^{1/2}$ of one another. For example, the following solvents and acetic acid have polar and H-bonding components, respectively, shown in parentheses: xylene (1.0, 3.1); anisole (4.1, 6.8); 2-propanol (6.0, 16); and acetic acid (8.0, 14).

Another measure of polarity is the dipole moment of the solvent. The term "dipole moment" refers generally to the polarity of molecules and, more particularly, is the product of the magnitude of the electric charges and the distance between it and its opposite charge in an electric dipole. Solvents of the present invention are preferably selected to have dipole moments such that suitable selectivity is achieved. In particular, preferred solvents have a dipole moment of greater than about 0.50 Debye, more preferably greater than about 0.75 Debye, and even more preferably greater than about 1.0 Debye.

Another measure of the polarity of a solvent is its dielectric constant. The dielectric constant of a substance refers to its ability to resist the transmission of an electrostatic force from one charged body to another. Solvents of the present invention are preferably selected to have dielectric constants such that suitable selectivity is achieved. In particular, preferred solvents have a dielectric constant greater than about 1.5, more preferably greater than about 2, and more preferably greater than about 3.

Suitable solvents for use in the present invention are organic or silicon-based solvents. For example, suitable solvents can include aromatic solvents, aliphatic solvents, ethers, ketones, silicon-based solvents and halogenated solvents. Preferred solvents are aromatic solvents.

Specific solvents of the present invention include 2-butanone, 2-heptanone, 2-hexanone, 2-pentanone, acetone, anisole, butyl ether, ethyl ether, isopropyl ether, methylphenyl ether, benzene, cumene, m-xylene, o-xylene, p-xylene, toluene, cyclohexane, heptane, hexane, nonane, octane, 1-pentene, 2-octanone, dimethyl sulfoxide, phenetole, 4-methyl anisole, 1,3-dimethoxybenzene, 1,2-dimethoxybenzene, dimethoxybenzene, 1,4-dimethoxybenzene, mesitylene, chlorobenzene, 1,2-dichlorobenzene, 1,3-dichlorobenzene, 1,4-dichlorobenzene, 2-chlorotoluene, 4-chlorotoluene, veratrole, and 3-chlorotoluene. Preferred solvents include toluene, xylene, anisole, phenetole, 4-methyl anisole, 1,3-dimethoxy benzene, and mesitylene. Particularly preferred solvents of the present invention include xylene, anisole and 4-methyl anisole.

Substituted aromatic solvents are particularly preferred for the present invention. Such solvents are typically polar and thus, provide high selectivity. For example, anisole is polar and provides very high selectivity. Also preferred are di-substituted aromatics, such as 4-methyl anisole.

By selecting solvents according to the parameters discussed above, high selectivities can be achieved. For example, selectivities of greater than about 30%, more preferably greater than about 50%, and even more preferably greater than about 70% can be achieved.

In a preferred embodiment of the present invention, solvents of the present invention can include a mixture of solvents which are independently in accordance with the present invention. For example, a mixture of solvents, each having different advantages, can be used. For example, a mixed solvent can include a polar solvent, such as anisole, to favor high selectivity. Such a mixture can also include a second solvent, such as xylene, which is relatively less polar, but which is particularly useful in recovery of XD because, upon cooling, the less polar solvent will phase separate from $X_1A$ and oligomers of $X_1A$ and XD, being less polar, will partition with the less polar solvent. Suitable mixtures of solvents can be selected by choosing one or more solvents from each of the following classes. More polar solvents can be selected from the group of anisole, 4-methyl anisole, 1,3-dimethoxybenzene and other similar solvents. Less polar solvents can be selected from the group of xylene, toluene, mesitylene and other similar solvents. In this embodiment, the less polar solvent can have a solubility for $X_1A$ of from about 2% to about 30% at about the boiling point of the production solvent and more preferably from about 5% to about 10% at about the boiling point of the production solvent. The more polar solvent has a solubility for $X_1A$ of greater than about 30% at about the boiling point of the production solvent and more preferably greater than about 50%.

Such mixed solvents can include wide ranges of the various components. For example, in a mixture as discussed above including a more polar and a less polar solvent, such as anisole and xylene, the solvents can be mixed in ratios preferably ranging from about 5:95 to about 50:50, and more preferably from about 10:90 to about 30:70. It should be noted that as the amount of polar solvent is increased, the selectivity will increase. However, as discussed above, it has been found that conversion can decrease with more polar solvents. Thus, at higher concentrations of more polar solvents, the possible decrease in conversion for a given reaction time can be offset by the use of higher catalyst concentrations.

Effect of Feed Concentration on Cyclic Ester Production

Another reaction parameter subject to control of the present invention is the production of cyclic esters with high selectivity by the use of low concentrations of reactant species in the feedstream. While not intending to be bound by theory, it is believed that lower feedstream concentrations are likely to favor the uni-molecular cyclic esterification of $X_2A$ to form XD over the dual-molecular linear esterification reaction of $X_2A$ with an $X_1A$ molecule to form $X_3A$. The probability of a successful linear esterification reaction depends on the frequency with which the linear ester ($X_2A$ or higher oligomer) encounters free $X_1A$ molecules or other linear oligomers in a suitable geometry. At lower $X_1A$ concentrations, the probability of linear esterification (i.e., oligomerization) is decreased. $X_2A$ to XD cyclic esterification, however, is not dependent on $X_1$ concentration because this esterification does not require the collision with an $X_1A$ molecule. Rather, the two ends of the $X_2A$ molecule must encounter each other in an appropriate conformation. Thus, the probability of a successful collision is dependent on the energy present in the system (which is experienced by molecular bending and rotations) but not on the concentration of reactant species once the $X_2A$ molecule is formed.

In particular, the method for attaining high selectivities with low reactant concentrations includes providing a feedstream which includes XA and a solvent, and removing water to produce cyclic esters. The concentration of XA in the feedstream is maintained low enough such that the concentration of $X_5A$ and higher oligomers in the reaction formed from the XA is less than about 20%. More preferably, the concentration of $X_5A$ and higher oligomers formed from the XA is maintained below about 15% and more preferably below about 10%. More particularly, the concentration of $X_1A$ and $X_2A$ in the feedstream is maintained not to exceed the solubility of the reactants for that solvent. More specifically, the concentration of $X_1A$ and $X_2A$ in the feedstream is maintained at less than about 95% of the solubility of $X_1A$ and $X_2A$ in the feedstream, more preferably less than about 50%, and even more preferably less than about 25%. In accordance with the above parameters regarding concentration of feedstream components, selectivities of greater than about 40%, more preferably greater than about 50%, and even more preferably greater than about 70%, can be achieved.

The present invention also includes the attainment of high conversion rates by providing a feedstream having a high concentration of XA. In this manner, the various reactive species in XA are more likely to react under a given set of conditions. High XA concentrations can be achieved by appropriate selection of reaction variables, such as solvent selection and pressures, as discussed elsewhere herein. Preferably, to achieve high conversion, a feedstream having an XA concentration (calculated on an $X_1A$ basis) of at least about 5 wt %, more preferably at least about 25 wt %, and even more preferably at least about 50 wt % can be used in the present process. Thus, it is also preferred that XA has a solubility in the production solvent of at least about 5% at about the production solvent's boiling point at atmospheric pressure, more preferably at least about 25%, and even more preferably at least about 50%.

It should be noted that, as discussed elsewhere herein, selectivity can be affected negatively by high reactant concentrations. Thus, the benefits of high conversion by use of high reactant concentrations, can be accommodated by use of other parameters to achieve acceptable selectivity rates. For example, by use of solvents having relatively high selectivity, the negative effect on selectivity by higher reactant concentrations may be acceptable.

Effect of Temperature on Cyclic Ester Production.

The temperature of the cyclic ester formation process controls both the rate of free water removal and the rate of esterification. The temperature of feedstream treatment for esterification and water removal, for a given set of other treatment parameters, is high enough for effective cyclic ester formation and not so high as to convert XA components into aldehydes, carbon monoxide or other degradation products. Preferably, the cyclic ester production temperature ranges from about 55° C. to about 250° C. More preferably the temperature is from about 60° C. to about 225° C. The choice of solvent, in part, determines the temperature of the reaction when the reaction is being conducted at the boiling point of the solvent.

In a preferred embodiment, a further aspect of the present invention is conducting the cyclic ester production process to achieve high conversion rates. One factor affecting conversion is the use of high reaction temperatures. As identified above, typical reaction temperatures can range from 55° C. to 250° C. To achieve high conversion rates, the reaction temperature can be conducted above about 110° C., more preferably above about 135° C., and more preferably above about 155° C.

Effect of Pressure on Cyclic Ester Production.

The pressure at which the cyclic ester formation process is conducted is also a reaction parameter to be controlled. For example, at higher pressures, higher reaction temperatures can be attained for a given solvent which results in faster reaction rates and, thus, higher conversion at fixed reaction times. Also, at these higher temperatures the solubility of XA components in solvents, particularly those in which XA has low solubility, is increased, resulting in higher conversion. The pressure, however, can be either atmospheric, greater than atmospheric or less than atmospheric. Preferred pressures of the present invention are atmospheric pressure and greater than atmospheric pressure.

Effect of Reaction Time on Cyclic Ester Production

The cyclic ester formation process can be conducted for varying times and typically is conducted until cyclic ester formation is substantially optimized. The reaction time will of course vary according to other parameters such as temperature and the presence of catalyst. For example, the formation of a cyclic ester such as lactide from commercial lactic acid diluted in toluene by removing water by heating from room temperature to the boiling point of toluene is substantially optimized within about 2 to about 5 hours in a batch reactor.

Effect of Catalysts on Cyclic Ester Production

There are many esterification catalysts for formation of XD which can be used in the present process including, but not limited to ion exchange acidic catalysts, such as Nafion and Dowex 50; soluble acidic catalysts, such as sulfuric acid, methanesulfonic acid, trifluoromethane sulfonic acid, and toluene sulfonic acid; silica-based catalysts, such as alumina-silicate; other solid heterogeneous acidic catalysts, such as alumina, eta-, theta-, delta- and gamma-alumina, silica, aluminum sulfate, lead oxide, antimony trioxide, beryllia, yttria; metal ester catalysts, such as stannous octoate and titanium tetra(isopropoxide); enzymes, such as hydrolases; zeolites; so-called template catalysts, such as di-n-butyltin oxide; micellar catalysts, including polar catalysts such as sulfosuccinate salts such as sodium di(2-ethylhexyl) sulfosuccinate sold as Aerosol OT by Pfizer; non-polar catalysts such as polyoxylethylene nonyl phenol, and phosphates. Preferred catalysts include zeolites and acidic catalysts, such as sulfuric acid, Dowex 50, gamma-alumina, and toluene sulfonic acid.

In a preferred embodiment of the present process, a zeolite catalyst is used as the esterification catalyst. Zeolite catalysts are solid catalysts which have porous structures with proton donating sites inside the pores. A preferred zeolite catalyst for the present invention is one having a proton donating site which is large enough to accommodate catalysis of $X_1A$ and $X_2A$ molecules, but not large enough to accommodate larger oligomers. In this manner, the zeolite catalyst will promote higher rates of selectivity. In addition, preferred zeolite catalysts require a low enough affinity with water to allow water to be removed from the reaction system, yet still have enough affinity for $X_1A$ and $X_2A$ to catalyze esterifications to $X_A$ and XD. The affinity for $X_1A$ and $X_2A$ must be balanced with the ability to reject XD once it is formed.

The amount of catalyst used in the present process will vary depending on treatment parameters, such as temperature and pressure, reactivity of the catalyst and the desired rate of reaction increase. Moreover, it will be recognized that the amount of any particular catalyst for a given system must account for, inter alia, the competition between esterification to produce a cyclic ester from $X_2A$ and esterification to produce higher oligomers from $X_2A$. Thus, depending on reaction kinetics and treatment of a feedstream, preferred amounts of catalyst for production of cyclic ester can be determined by those skilled in the art.

Catalyst concentration can be controlled to achieve high conversion rates. In addition, it has been found that some solvents which provide high selectivity, i.e., more polar solvents, are reactive with some preferred catalysts, such as sulfate type catalysts. Thus, such solvents can deplete catalyst levels resulting in poorer conversion. Therefore, when using such solvents and catalysts, particularly high catalyst concentrations are needed to achieve high conversion rates. For example, in the case of a sulfuric acid catalyst and other similar catalysts, when used in conjunction with a polar solvent such as anisole, 4-methyl anisole and 1,3-dimethoxybenzene, catalyst concentrations are at least about twice as much, more preferably at least about five times as much, and even more preferably at least about ten times as much as the general catalyst concentration parameters discussed above. Conversely, solvents which are less reactive with catalysts are particularly useful to achieve high conversions. For example, xylene, toluene and mesitylene are useful to achieve high conversion rates in sulfuric acid-catalyst systems because they are relatively non-reactive.

Use of certain catalysts and other reaction parameters can be controlled to achieve a desired meso-cyclic ester product. For example, with regard to a cyclic ester such as lactide, lactide has two asymmetric carbon atoms so it may be obtained in three stereoisomeric forms: L-lactide in which both asymmetric carbon atoms possess the L (or S) configuration; D-lactide in which both asymmetric carbon atoms possess the D (or R) configuration; and meso-lactide in which one asymmetric carbon atom has the L-configuration and the other has the D-configuration. L-lactide and D-lactide are enantiomers while meso-lactide is a diastereomer of L-lactide and D-lactide in which the methyl groups are trans to each other in the dioxanedione ring. Maintenance of the chirality in L-lactic acid will lead exclusively to the formation of L-lactide which has utility in the production of degradable polymers. However, racemization of the chirality originally in L-lactic acid will lead to the production of meso-lactide which also has a key utility as a comonomer with L-lactide in the production of degradable polymers. By variation of the conditions and catalysts used in each of the embodiments described for this invention, the lactide obtained from L-lactic acid feedstock, or feedstream, may be either nearly exclusive L-lactide or it may contain controlled quantities of meso-lactide and D-lactide in addition to L-lactide.

Racemization of lactic acid or other $X_1A$ species may be carried out by a process called the Walden Rearrangement. In this process, the a-OH group is substituted by a halogen or other suitable leaving group in such a manner that the relative configuration around the a carbon is preserved. This is accomplished by treatment with suitable reagents such as phosphorous pentachloride or thionyl chloride. Lactic acid is regenerated from the resulting halo-acid by resubstituting the halogen group with OH usually with potassium hydroxide. In this substitution, however, the configuration around the a carbon is inverted resulting in a lactic acid molecule of opposite configuration from the original.

Alternatively, racemization can take place by dehydrating lactic acid under vigorous conditions, usually with strong base, (this treatment involves the formation of a double bond between the α and methyl carbon and not esterification) then rehydration to regenerate lactic acid. This hydration results in a random mixture of L- and D-isomers.

Racemic mixtures of L- and D- isomers of XA can also be prepared by production of XA by microorganisms which produce racemic mixtures of XA. Further, racemic mixtures can be provided by mixing of commercially available sources of L- and D- isomers.

Conversion and Productivity in Cyclic Ester Production

As noted elsewhere herein, various aspects of the present invention include the use of process parameters to achieve high conversion. By use of appropriate process parameters in accordance with the present invention, conversion of at least about 30% can be achieved, more preferably at least about 70% and even more preferably at least about 90%.

A further aspect of the invention resulting from attainment of both high selectivity and conversion is high productivity. Thus, by appropriate selection of process parameters discussed herein, productivity of at least about 25% can be achieved, more preferably at least about 50% and even more preferably at least about 80%.

REACTION CONFIGURATIONS FOR THE PRODUCTION OF CYCLIC ESTERS

A further aspect of the present invention concerns the use of various reaction vessel configurations that are suitable and particularly useful in conducting processes of the present invention. Cyclic ester production in accordance with the present invention can be suitably performed in batch, fed-batch or continuous reactors. In addition, continuous reactors can be of continuous stirred tank reactor (CSTR) design or a plug flow reactor design. It should be further noted that various configurations of different reactor types and numbers can be advantageously used to improve productivity, selectivity and/or volumetric efficiency. Volumetric efficiency means the rate of production of XD per unit volume per unit time. A higher volumetric efficiency means that smaller and therefore less costly equipment can be used for a given overall XD production rate.

Batch reactors are well known in the chemical industry. The control of reaction parameters such as temperature, pressure, removal of vapor, control of concentration and the addition and removal of reactants and products are well known to those skilled in the art. The usefulness of control of these reaction parameters has been discussed elsewhere.

One particularly useful type of batch reaction for the present invention is the use of a fed batch reactor. In this type of reactor, the initial charge of reaction mixture prepared according to the present invention is allowed to react for a period of time. Some free volume must exist in the reactor. It should be noted that as the reaction progresses and the esterification reactions take place, XA and in particular $X_1A$ and $X_2A$ are depleted. In this manner, as the concentration of XA decreases, the reactants in the XA mixture available for conversion and production into cyclic esters are reduced. Therefore, the overall production of XD for a given time period can be increased if the XA which is converted is replenished. Thus, it is an aspect of the present invention that the concentration of $X_1A$ and $X_2A$ are maintained at about 70% of the initial concentration level, more preferably above about 80% of the initial concentration level, and even more preferably above about 90% of the initial concentration level. Maintenance of $X_1A$ and $X_2A$ within the parameters discussed above can be accomplished in various ways. For example, an additional or make-up feedstream can be introduced into the XD reaction vessel. When the reaction has been carried out to the desired extent, the entire reaction mixture can be removed from the reactor and processed to recover the XD product. The XD product prepared by the fed batch process will be more concentrated in the reaction mixture compared to the batch reaction, thus improving recovery efficiency. The control of concentration can improve selectivity as discussed elsewhere. And the use of fed batch can improve volumetric efficiency of the reactor.

The use of continuous processes in the chemical industry has many advantages in improving process efficiency. It has been found that the present invention can be advantageously carried out in a continuous process. It has been discovered that there are particularly advantageous reactor configurations for the process of the present invention.

One advantageous reactor configuration is the use of two or more sequential continuous reactors, including but not limited to, sequential CSTR's. Another reactor configuration is a plug flow reactor in which the reaction mixture flows with minimum back mixing along the length of the reaction vessel. The physical design of these reactors is well known to those skilled in the art.

In one embodiment of the present invention the process can be conducted in a configuration of two or more sequential continuous reactors. A suitable equipment set- up is discussed below in Example 13.1. By conducting the process in this manner, it has been found that the productivity of the process can be increased compared to conducting the reaction in a single continuous reactor. In particular, it has been found that high volumetric efficiencies can be achieved with using two or more continuous reactors. For example, volumetric efficiencies of greater than about 10 g/l/hr, more preferably greater than 25 g/l/hr, and even more preferably greater than about 35 g/l/hr.

One embodiment of the staged continuous reactor configuration is based on the recognition that as an XA feedstream is reacted to form XD, a first stage of reaction occurs during which $X_2A$ molecules are formed from $X_1A$ molecules and a second stage occurs during which $X_2A$ molecules are reacted to form XD. In the first stage, relatively high feedstream concentrations promote the conversion of $X_1A$ molecules to XA molecules due to the intermolecular nature of the reaction. The second stage of the preferred reaction, however, is the intramolecular reaction of $X_2A$ to XD. As noted above, lower concentrations of reactive components favor cyclization, while higher concentrations favor the formation of higher oligomers.

Thus, this two-stage production process embodiment of the invention includes providing a feedstream of XA having a relatively high concentration of $X_1A$ to promote the formation of $X_2A$ molecules. Subsequently, the concentration of the feedstream is reduced prior to significant formation of $X_3A$ and higher oligomers, thereby, selecting for cyclization of $X_2A$ molecules. More particularly, this embodiment includes providing a feedstream of XA wherein the proportion of $X_1A$ to all potentially reactive species (all species expressed as $X_1A$ equivalents) is at least about 80%, more preferably at least about 90%, and even more preferably approaching 100%. The feedstream is then reacted under esterification conditions to form $X_2A$. Preferably, the process is conducted until the proportion of $X_2A$ to all potentially reactive species is at least about 35%, more preferably at least about 50%, and even more preferably at least about 75%. Alternately, the reaction can be continued until the proportion of $X_3A$ and higher oligomers to all potentially reactive species approaches about 35%, more preferably approaches about 25%, and even more preferably approaches about 20%. At this stage, the concentration of the intermediate stream is reduced to a concentration of reactive components that is suitable to promote high selectivity. This reduction can be accomplished by the addition of more solvent of either the same type of a different type. For example, the production of $X_2A$ might be accomplished in an aqueous phase while the reaction to XD might be accomplished in an organic phase or, alternatively, two different organic solvents can be used. Typically, the concentration is reduced to a concentration of $X_2A$ which is at or below the solubility limit of $X_2A$ in the second stage of the system. The reaction is then maintained under esterification conditions to form XD.

In a further embodiment of the staged reactor configuration, the first stage effectively removes the majority of any water initially present in the incoming XA feedstream. Subsequently, as the reaction mixture is transferred to the second and any subsequent reactors, the cyclic ester production reaction can take place in the absence of significant amounts of water, which otherwise could possibly reverse the cyclic ester production reaction. The concentration of water in the feedstream as it exits the first reaction vessel is preferably less than about 12 wt %, more preferably less than about 1 wt %, and even more preferably less than about 0.5 wt %. As noted, in a staged continuous reaction set-up, two or more vessels are used, and most preferably two or three.

In the embodiment discussed above the dehydration function of the first reactor can be accomplished with a variety of reactor types, including a plug flow reactor such as a water stripping column, and a CSTR, with a water stripping column preferred. Various types of water stripping columns are suitable for use. For example, packed columns, using high surface area and inert packing materials can be used. Alternatively, columns with perforated plates, valve trays or bubble caps can be used. Water removal is readily achieved in columns, as opposed to in a CSTR because of better mass transfer and heat transfer characteristics in a column. In addition, columns are more suited for removal of water than other standard plug flow reactors in which release of water from the reaction vessel is more complicated. After water initially present in the XA stream, and any water generated by formation of XD, is removed from the feedstream in the column, depending on desired residence time in the column, the reaction mixture can be transferred to a CSTR. A suitable reaction vessel configuration including a column and two CSTRs is discussed in Example 13.2.

In the above embodiment when a water stripping column is used as a first reactor, with subsequent CSTR, when water is removed from the feedstream and the product is subsequently fed to a CSTR, $X_1A$ may be lost if water is completely stripped because many $X_1A$'s form azeotropes with water. It has been found that the present invention advantageously overcomes this limitation by the appropriate use of the reaction solvent. If solvent vapors are allowed to enter the stripping column and condense, forming a reflux flow, the column may be controlled in such a manner as to produce an anhydrous reaction mixture and prevent $X_1A$ from being lost overhead in the column. The use of any production solvent with a boiling point lower than the $X_1A$ will allow this advantageous result in the stripping column.

A further advantageous reactor configuration has been discovered for carrying out the present invention. The use of sequential reaction stages has been discussed as providing advantages in productivity, selectivity and volumetric efficiency. It has been found that all of these advantages can be obtained by the use of a single continuous reaction vessel in the form of a distillation column. Such a column is referred to as a reactive distillation column.

A reactive distillation column can be used to carry out the various desired features of the present invention. In one embodiment, XA is fed near the top of the column with the production solvent. The top stages are used to dehydrate the feedstream, and return $X_1A$ to the column. As the reaction mixture flows down the column to the lower stages, it is continuously contacted by solvent vapor flow coming up the column. At an appropriate point, a catalyst may be introduced into the anhydrous reaction mixture. The reaction mixture is maintained under reaction conditions suitable for the conversion of $X_1A$ to $X_2A$ and subsequently to XD. Other feedstreams containing $X_1A$ may be introduced at various points to maintain $X_1A$ concentration at a desired level. At an appropriate residence time, the reaction mixture flows from the bottom of the column and to the recovery process for XD. Residence time in the column may be controlled by appropriate design considerations. The use of deep multipass bubble cap trays allows large liquid hold up and therefore, longer residence time for the reaction mixture without increasing the required solvent boilup rate. Solvent boilup rate is controlled to provide enough solvent vapor to carry the heat required to remove the water up the column. Residence time may also be controlled by the use of intermediate or subsequent CSTR's. For example, a side stream may be removed from the bottom section of the column, fed to a CSTR where it is held for a period of time, and then returned to the same or lower stage of the column. Alternatively, the reaction mixture as it flows from the bottom of the column may be conducted to a CSTR where it can be held for a period of time for further reaction to take place before it is sent on to the XD recovery process.

The use of a reactive distillation process has been found to have various advantages for the practice of the current invention. Distillation columns provide for excellent mass and heat transfer and this has been found to increase the water removal rate and thus the reaction conversion rate of $X_1A$. Removal of water along the entire length of the reactor is possible in a column and this provides a means to provide a plug flow reactor of simple design as opposed to a series of CSTR's. Such a reactive distillation column is truly continuous. A true plug flow reactor with potential for intermediate feeds has high volumetric efficiency.

RECOVERY AND PURIFICATION OF CYCLIC ESTERS

The cyclic ester production process described above yields a dilute solution of XD in solvent and other components. An objective of the present invention is to provide a means for the recovery and purification of XD to enable its use as a reaction feed material for example, as a monomer in the production of polymers. Several preferred embodiments for the recovery and purification of XD are described below. An inherent advantage of these embodiments is their integration with the cyclic ester production process. In accordance with the present invention, the reaction mixture containing XD is treated to recover and purify XD.

The present invention includes two methods to recover XD. In the first, the cyclic ester production process is performed in such a manner as to cause the reaction mixture, in the recovery process, to form two liquid phases in equilibrium to substantially separate XD from other components. This separation is a unique and novel technique. In the second, the cyclic ester production process is performed in such a manner as to yield a homogeneous reaction mixture which is then subjected to subsequent recovery steps.

The present invention further includes two methods to purify the XD obtained from the recovery step. The feed to the purification methods can be obtained by any of the embodiments of either recovery process. In the first method to purify XD, distillation serves as the predominant mechanism to separate XD from other components. In the second, crystallization techniques (melt or solvent crystallization)

serve as the predominant separation techniques. Surprisingly, one is able to use melt crystallization as a suitable and preferred method to purify XD. Furthermore, this technique produces high purity XD without degradation in the presence of oligomers and optical isomers of XD. In practice, combinations of these purification methods are employed as detailed below.

In a preferred set of embodiments, the recovery operation utilizing liquid-liquid equilibrium separation is accomplished by allowing phase separation in which one phase contains predominantly the cyclic esters and solvent and a second phase predominantly contains the $X_1A$ and oligomers of $X_1A$. The method includes providing a recovery solvent for the cyclic ester production mixture. The solution is then allowed to phase separate into a first phase which includes cyclic esters and the recovery solvent and a second phase which includes $X_1A$ and oligomers of $X_1A$. It should be noted that the second phase can either include a second phase solvent or consist primarily of $X_1A$. Cyclic esters are then recovered from the first phase. The cyclic ester production mixture can further include soluble esterification catalysts, such as sulfuric acid, which preferably partitions into the second phase. In this manner, the catalyst is readily separated from the cyclic ester.

The step of providing a recovery solvent for the cyclic ester production mixture can be accomplished in various ways. For example, cyclic esters can be produced in a reaction mixture which includes a reaction solvent that is also suitable for use as a recovery solvent. In the case where mixed solvents are used, the ratio of more polar to less polar solvents is adjusted to maximize reaction selectivity while maintaining a phase split upon cooling the reaction mixture. This phase split allows for the separation of solvents and cyclic esters to one phase and $X_1A$ and oligomers to the other phase. Alternatively, after cyclic ester production, a recovery solvent can be mixed in with a cyclic ester production mixture for purposes of cyclic ester recovery. This embodiment is a solvent extraction process for the recovery of XD.

The recovery solvent of this embodiment of the present invention is characterized in that cyclic esters partition preferentially into the recovery solvent. As discussed below, recovery solvents are relatively less polar. Thus, XD species, such as lactide, are more soluble in such solvents than the corresponding $X_1A$ species, such as lactic acid. In this manner, upon phase separation, the cyclic esters partition primarily to the recovery solvent phase. Preferably, the cyclic ester has a separation factor of at least about 1, more preferably at least about 5, and even more preferably at least about 15 in the recovery solvent at about room temperature at 1 atm. Separation factor is defined as the ratio of the distribution coefficient of XD divided by the distribution coefficient of the species in question, for example $X_1A$.

In a further embodiment, the separation factor can be controlled by varying the temperature at which the phase split is allowed to occur. For example, in a lactide/xylene system, at 40° C., the separation factor between lactide and lactic acid is 35, whereas, at 70° C., the separation factor drops to 26. However, at lower temperatures, the $X_nA$ and XD species tend to partition more into the non-solvent phase. Therefore, a key to the successful practice of the invention is the optimization of temperature.

Any solvent having suitable characteristics in accordance with the above-described functional parameters for a recovery solvent is suitable for use in the present process. More particularly, suitable recovery solvents include xylene, toluene, benzene, MIBK, and isopropyl ether, more preferred recovery solvents include xylene and toluene, with xylene being even more preferred.

The step of allowing phase separation of the cyclic ester production mixture into first and second phases is typically accomplished simply by allowing the mixture to cool with the cessation of any mixing or other agitation. This method can be done either batch or continuously using standard phase separation equipment known to those skilled in the art.

In addition to separating cyclic esters and solvent from $X_1A$ and oligomers of $X_1A$ by allowing phase separation, as an alternative embodiment, an additional solvent extraction step can be conducted on the second phase which is rich in $X_1A$ and oligomers of $X_1A$. This solvent extraction step is done to recover cyclic esters and solvent which remain in the second phase. For example, solvent, which is typically the recovery solvent, and the second phase are introduced into an extraction unit to recover residual cyclic ester and solvent in the second phase. Two streams exit the extraction unit. The first is rich in $X_1A$ and oligomers of $X_1A$. This stream can be recycled for further cyclic ester production, for example, through a hydrolysis reactor to hydrolyze oligomers back to $X_1A$ units. The second stream exiting the extraction unit is the cyclic ester and solvent fraction. This stream can be recycled to the incoming stream to the phase separation unit or, alternatively, combined with the first phase from the phase separation unit which is rich in cyclic ester and solvent for further processing.

A further alternative embodiment of cyclic ester recovery by liquid-liquid equilibrium separation involves the use of a reflux extractor to accomplish the liquid-liquid equilibrium separation rather than a phase separator. In this process, the cyclic ester production mixture is fed to an intermediate point within a refluxed extractor system. The extractor additionally has incoming recovery solvent, which is preferably the solvent in the cyclic ester production mixture, and a reflux stream having $X_1A$ and oligomers of $X_1A$ from subsequent cyclic ester purification. This reflux stream typically includes centrate from centrifugation of crystallized cyclic ester. Within the extraction unit, cyclic ester in the cyclic ester production mixture is partitioned into the solvent phase and $X_1A$ and oligomers of $X_1A$ partition away from the solvent. The outgoing stream containing $X_1A$ and oligomers of $X_1A$ can then be recycled for further cyclic ester production, for example, through a hydrolysis reactor to hydrolyze oligomers back to $X_1A$ units. The outgoing stream containing cyclic ester and solvent phase is then conducted for further processing.

A further alternative embodiment of the present cyclic ester recovery process includes conducting a cyclic ester production mixture directly from cyclic ester production operations to cyclic ester recovery, as discussed below, without first conducting a liquid-liquid equilibrium separation. In this process, the homogeneous reaction mixture is conducted directly to further XD recovery and purification operations. This process is particularly suitable for operations in which cyclic ester is produced in a more polar solvent. For example, if the cyclic ester production mixture includes anisole as a solvent, separate formation of an $X_1A$ phase does not occur.

Typically, the cyclic ester and solvent rich phase produced by the liquid-liquid equilibrium separations or the homogeneous reaction mixture is conducted for additional cyclic ester recovery. The stream can be first run through an evaporator unit in which solvent is driven off. Typically, enough solvent is driven off so that the remaining cyclic ester mixture includes between about 1% and about 80% by weight solvent, more preferably between about 5 and about 50 weight percent solvent, and even more preferably between about 15 and about 30 weight percent solvent. Solvent which is removed can be recycled back to other stages in the overall process, including recovery of $X_1A$ prior to cyclic ester production or directly back to cyclic ester production operations. Such solvent can also be brought forward for use in subsequent recovery or purification operations, such as solvent crystallizations. After exiting the evaporator unit, the cyclic ester-containing stream can be cooled prior to additional cyclic ester recovery or purification operations.

Further purification of the recovered XD stream can be carried out using distillation, solvent crystallization, and melt crystallization. Combinations of one or more of these methods may be required to economically produce high purity XD products. In addition, with proper sequencing of these methods it is possible to continuously produce two or more high purity XD products containing different ratios of optical isomers of XD. This result is particularly useful since the two XD products can be blended to give control over the optical isomer content in the polymer backbone of polymers based on XD. Such control is needed since many physical and degradation properties of some XD based polymers are strongly influenced by the optical isomer content in the polymer backbone.

The first step in the distillation process selectively distills $X_1A$ and solvent from the cyclic ester production mixture to form a mixture of cyclic ester and oligomers of $X_1A$. This mixture is then treated to selectively distill cyclic ester from the mixture. The vaporized cyclic ester is then recovered. The feed from the previously outlined recovery steps is then directed to, for example, a distillation column in which $X_1A$ and solvent are selectively vaporized from the cyclic ester production mixture. Thus, the $X_1A$ and solvent go overhead on the distillation column while the cyclic ester and higher oligomers of $X_1A$ exit through the bottom of the column. $X_1A$ and solvent removed from the mixture by this process can be recycled to earlier segments of the overall process. For example, $X_nA$ can be recycled to cyclic ester production. Solvent can be recycled either to $X_1A$ recovery operations, cyclic ester production operations or used for subsequent solvent extraction steps.

The underflow from the first distillation step is then conducted to a second step. The distillation column is run under conditions such that cyclic ester is selectively vaporized from the mixture of cyclic ester and oligomers of $X_1A$. Thus, the underflow from the distillation column contains primarily oligomers of $X_1A$ which can be recycled in the process subsequent to hydrolysis back to $X_1A$ units. Alternatively, this underflow stream can be sent back into the liquid-liquid equilibrium separation of XD recovery in order to recover residual XD. Cyclic esters in the overhead flow from the second distillation unit can then be subsequently purified by other methods, such by crystallization. The need for the final polishing steps by crystallization depends upon both the efficiency of the distillation step and the purity specification that the XD product must meet. For example, if polymerization grade XD is required, then the distillation specifications will require very high reflux ratios to meet XD product specifications if no crystallization polishing steps are used. However, adding the crystallization steps greatly reduces the reflux ratio requirements of the distillation while still meeting the high purity specifications of monomer grade XD.

It should be noted that the vaporization steps in this process can be conducted under vacuum to get acceptable recovery. Moreover, while this process can be readily conducted when $X_1A$ is $L_1A$ and XD is LD, with higher molecular weight species, the amount of vacuum needed for vaporization of $X_1A$ and XD may be greater than is practical.

Cyclic ester recovery operations can also include crystallization of cyclic esters which are then separated from non-crystallized species. In one embodiment of the additional cyclic ester purification operations, cyclic ester is recovered by solvent crystallization. Solvent used in solvent crystallization performs a number of functions during the crystallization process. By use of a solvent, crystallization can be conducted at lower temperatures than if no solvent is present. In addition, the presence of solvent reduces viscosity of the system thereby making material handling and pumping easier. Further, the presence of the solvent can result in a purer crystallization process by providing a medium to contain impurities such as $X_1A$ and oligomers of $X_1A$ during crystallization. Thus, upon subsequent separation of crystals from the crystallization mixture, impurities such as $X_1A$ and oligomers of $X_1A$ can more readily separate with the liquid stream, rather than adhering to crystals.

In solvent crystallization, a feedstream containing cyclic ester and solvent is conducted to a crystallization loop. Conventional crystallization equipment can be used in this process. The stream containing cyclic ester and solvent is conducted through a crystallizer which functions to remove heat from the stream to induce crystallization. For example, a scraped surface heat exchanger can be used in which a crystallization chamber is cooled by a jacket containing cooling fluid. The crystallization chamber includes scrapers to remove crystals formed on the walls of the chamber. The stream is circulated from the crystallizer to a growth tank which serves as a reservoir for increasing and controlling residence time of material in the crystallization loop. Residence times in the loop are desired to be maintained as low as possible while still achieving adequate crystal size. Typically the residence times are from about 1/12 to about 6 hours, more preferably from about 1/6 to about 3 hours, and even more preferably from about 1/4 to about 1 hour. The growth tank additionally can include agitation of the material in the growth tank to achieve uniform mixing of the material in the growth tank. Material from the growth tank is then subsequently conducted back to the crystallization unit.

A side stream is removed from the loop or growth tank which contains crystallized cyclic ester, solvent, uncrystallized cyclic ester and impurities, including $X_1A$ and oligomers of $X_1A$. The side stream is then treated to remove the solid crystals from the stream. Removal of the crystallized cyclic ester can be conducted by any conventional technique known to those skilled in the art. Such techniques include centrifugation, filtration, and use of cyclones. Centrifugation of the crystals is preferred. Upon removal of cyclic ester crystals, a cyclic ester crystal cake and a liquid stream are produced. The cake can constitute a final product or, as discussed below, be further processed for additional purification. The liquid stream resulting from centrifugation or centrate of cyclic ester crystals can be further treated for additional recovery of cyclic esters from the liquid stream. Additionally, the liquid stream can be treated for recycle of $X_1A$ and oligomers of $X_1A$ present in the liquid.

After a single crystallization step, cyclic ester purities are typically at least about 80 weight percent, more preferably at least about 85 weight percent, and even more preferably at least about 90 weight percent cyclic ester on a solvent-free basis. Typical impurities are $X_1A$, oligomers of $X_1A$, and solvent.

Additional crystallization can be conducted on the recovered cyclic ester crystals from a first crystallization process to obtain more pure crystals. Subsequent crystallizations can be either solvent crystallizations or melt crystallizations. After a second crystallization, cyclic ester purities are typically at least about 95 weight percent, more preferably at least about 97 weight percent, and even more preferably at least about 98 weight percent on a solvent-free basis. After a third crystallization step, cyclic ester purities are typically in excess of 99 weight percent cyclic ester on a solvent-free basis. If a second or third crystallization is a solvent crystallization process, the cyclic ester crystal cake recovered from, for example, a centrifugation recovery, is dissolved in solvent with the help of agitation and/or mild warming. The dissolved cyclic ester is then conducted through a solvent crystallization loop, as described above.

A further novel aspect of the present invention is the recovery of cyclic esters by melt crystallization. In this process, cyclic ester crystals are subjected to temperatures sufficient to melt the cyclic ester cake. The melted material is then conducted to a crystallization loop, as discussed above. It should be noted that melt crystallization has a number of particular advantages over solvent crystallization processes. For example, because the volume of material being handled is significantly smaller in the absence of a solvent, smaller sized equipment is needed to obtain the same production. Additionally, because solvent does not have to be handled and removed from the system, the overall energy requirements for melt crystallization are lower. In addition, it has been found that larger crystal sizes are obtained by melt crystallization. Larger crystals are typically more pure than smaller crystals due to higher volume to surface ratios, thereby reducing surface area available for adherence of impurities.

Residence times in the crystallization loop for melt crystallizations are typically somewhat longer than those for solvent crystallizations. For example, residence times are typically from about 1/12 to about 6 hours, more preferably from about 1/4 to about 4 hours, and even more preferably from about 1/2 to about 2 hours. The temperature of the crystallization melt is typically maintained at a temperature between the melting temperature of the material and about 20° C. less than the melting temperature of the material. The optimal operation temperature depends upon the amount of solids present in the slurry at the given operating temperature. Typically, solids handling equipment (pumps, scraped surface heat exchangers, centrifuges, etc.) work best with solid loadings around 20 to 30 weight percent although slurries as low as one weight percent and as high as 60 weight percent can be handled.

As discussed above with regard to solvent crystallization, a side stream is removed from the crystallization loop and conducted to a unit for separation of cyclic ester crystals from impurities and non-crystallized cyclic esters. The impurities and non-crystallized cyclic esters can be recycled for further processing, for example, as an incoming feed to a first crystallization unit.

A further embodiment of the present invention is the recovery of cyclic ester from a cyclic ester production mixture which includes more than one isomeric species of cyclic ester, $X_1A$ and oligomers of $X_1A$. This process includes selectively crystallizing one of the isomeric species as cyclic ester and recovering that isomeric species. The process then includes crystallizing the second isomeric species and recovering it. This recovery method is suitable when $X_1A$ is a chiral molecule and, thus, has isomeric forms. For example, lactic acid is a chiral species of $X_1A$. There exist two optical isomers of lactic acid, L-lactic acid and D-lactic acid. Consequently, lactide can be either L-LD (a lactide molecule formed from two L-lactic acid molecules), D-LD (a lactide molecule formed from two D-lactic acid molecules), meso-LD (a lactide molecule formed from one L-lactic acid molecule and one D-lactic acid molecule), or D,L-LD (an intermolecular species consisting of one L-LD molecule and one D-LD molecule ). The different species of lactide have different melting points. Meso-LD has the lowest melting point of 52.8° C., isomerically pure D-LD and L-LD both have melting points of 98.7° C., and pure D,L-LD has the highest melting point of 128° C.

For example, isomeric species of a given XD molecule having higher melting points than other isomeric species can be selectively crystallized during a melt crystallization process. By forming a melt of the entire cyclic ester mixture, and crystallizing the higher melting point species at a temperature above the melting point of the lower melting point cyclic ester species, the higher melting point species can be selectively crystallized. Subsequently, upon recovery of the crystals, for example, by centrifugation, the resulting centrate will have the lower melting point isomeric species plus residual amounts of the higher melting point isomeric species. The cake from this crystallization can be potentially used as one of the two XD feeds to an XD polymerization step. The other feed to the XD polymerization step could be obtained by a solvent crystallization of the centrate from the melt crystallization. When a crystallization solvent is used that exhibits low isomeric selectivity, for example, toluene, the XD produced by the solvent crystallization step has a significantly different isomeric content than the XD produced by melt crystallization. It should be noted that selective crystallization, as discussed above, will not achieve 100% selectivity. Thus, in the example discussed above, the first crystallized fraction may contain residual amounts of the lower melting point species. Likewise, the second crystallized fraction will contain significant amounts of the higher melting point species. However, as long as the desired ratio of optical isomers in the polymer backbone is between the contents of the two XD products, a simple blending operation can be used to adjust the actual ratio of optical isomers. This is significant since it allows for the control over the optical isomer content of the XD based polymers, which is what controls the physical and degradation properties of many XD based polymers.

The following examples show how the present invention has been practiced, but should not be construed as limiting.

EXAMPLES

Example 1

This example examines the effect of solvent polarity on productivity, conversion, and selectivity of lactide formation from lactic acid according to the present invention by comparison of the solvents anisole, xylene, phenetole, 4-methyl anisole and 1,3-dimethyl benzene.

A 500 mL round-bottomed three necked flask equipped with a Dean-Stark trap, condenser, thermometer, and sampling septum was charged with 190 mL of solvent and heated to reflux. To the heated solution was added 10 mL of 88% aqueous lactic acid and 0.2% sulfuric acid by weight of XA feed. The reaction mixture was heated at reflux for 6 hours. After 220 minutes, a 0.1 mL sample was removed and analyzed for lactide content by HPLC. The results are shown below in Table 1 and illustrated in FIG. 1.

TABLE 1

Effect of Solvent Polarity on Lactide Production

| Solvent | Selectivity | Conversion | Productivity |
|---|---|---|---|
| Anisole | .77 | .35 | .27 |
| Xylene | .40 | .89 | .36 |
| Phenetole | .82 | .42 | .35 |
| 4-Methyl Anisole | .73 | .69 | .50 |
| 1,3-Dimethoxy Benzene | .45 | .95 | .45 |

The foregoing results indicate that more polar solvents have higher selectivity than less polar solvents. Conversion is highest with solvents which are disubstituted aromatics. Productivity is highest with 4-methyl anisole.

Example 2

This example examines the effect of varying sulfuric acid catalyst concentration in the preparation of lactide from lactic acid in anisole according the present invention to evaluate the effect of catalyst concentration on productivity, conversion, and selectivity.

Figure 2:
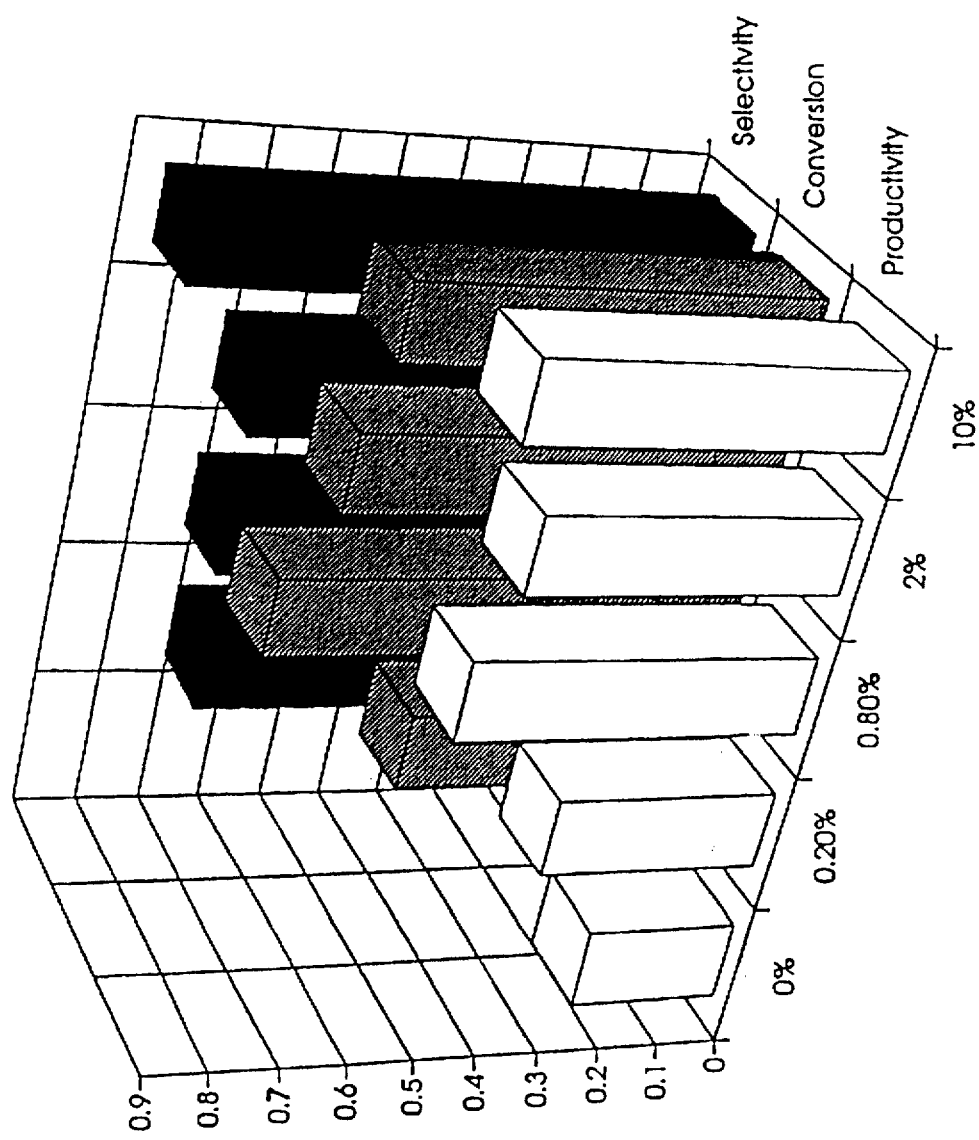
FIG. 2 is a three-dimensional representation of the selectivity, conversion and productivity in the production of lactide in anisole using different concentrations of sulfuric acid catalyst.

A 500 mL round-bottomed three necked flask equipped with a Dean-Stark trap, condenser, thermometer, and sampling septum was charged with 190 mL of solvent and heated to reflux. To the heated solution was added 10 mL of 88% aqueous lactic acid and either no catalyst, 0.2%, 0.8%, 2.0%, or 10% sulfuric acid by weight of XA feed. The reaction mixture was heated at reflux for 6 hours. After 290 minutes, a 0.1 mL sample was removed and analyzed for lactide content by HPLC. The results are shown below in Table 2 and illustrated in FIG. 2.

TABLE 2

Effect of Catalyst Concentration on Lactide Production with Anisole

| Sulfuric Acid Concentration (wt %) | Selectivity | Conversion | Productivity |
|---|---|---|---|
| 0 | NA | NA | .24 |
| 0.2 | .72 | .49 | .35 |
| 0.8 | .73 | .74 | .54 |
| 2.0 | .73 | .67 | .49 |
| 10.0 | .86 | .64 | .55 |

The foregoing results indicate that conversion, selectivity and productivity tend to increase with increased catalyst when using a relatively polar solvent, such as anisole, although at higher levels, 0.80% and above, productivity tends to level off. At the highest level of catalyst, 10%, selectivity increased slightly.

Example 3

This example examines the effect of varying sulfuric acid catalyst concentration in the preparation of lactide from lactic acid in xylene according the present invention to evaluate the effect of catalyst concentration on productivity, conversion, and selectivity.

Figure 3:
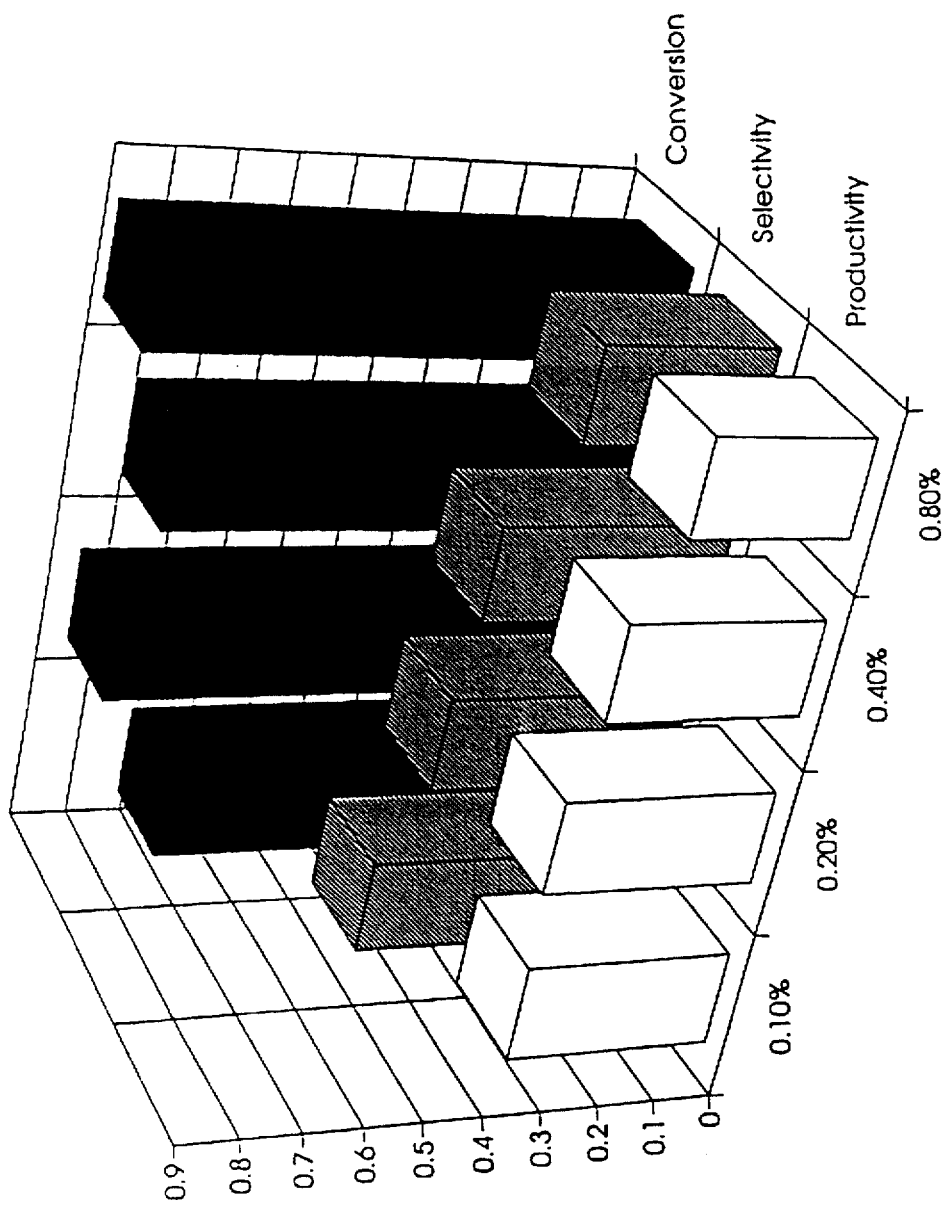
FIG. 3 is a three-dimensional representation of the conversion, selectivity and productivity in the production of lactide in xylene using four different concentrations of sulfuric acid catalyst.

A 500 mL round-bottomed three necked flask equipped with a Dean-Stark trap, condenser, thermometer, and sampling septum was charged with 190 mL of xylene and heated to reflux. To the heated solution was added 10 mL of 88% aqueous lactic acid and either no catalyst, 0.1%, 0.2%, 0.4%, or 0.8% sulfuric acid by weight of XA feed. The reaction mixture was heated at reflux for 6 hours. After 96 minutes a 0.1 mL sample was removed and analyzed for lactide content by HPLC. The results are shown below in Table 3 and illustrated in FIG. 3.

TABLE 3

Effect of Catalyst Concentration on Lactide Production with Xylene

| Sulfuric Acid Concentration (wt %) | Selectivity | Conversion | Productivity |
|---|---|---|---|
| 0.1 | .49 | .73 | .35 |
| 0.2 | .42 | .87 | .36 |
| 0.4 | .40 | .82 | .33 |
| 0.8 | .30 | .90 | .27 |

The results of this example illustrate that high conversion rates can be achieved in xylene at increasingly high catalyst concentrations. Moreover, overall productivity was maximized at a catalyst concentration of 0.2%.

Example 4

This example examines the use of a high level of catalyst with xylene as a solvent in the production of lactide from lactic acid and the effect on conversion, selectivity and productivity.

Figure 4:
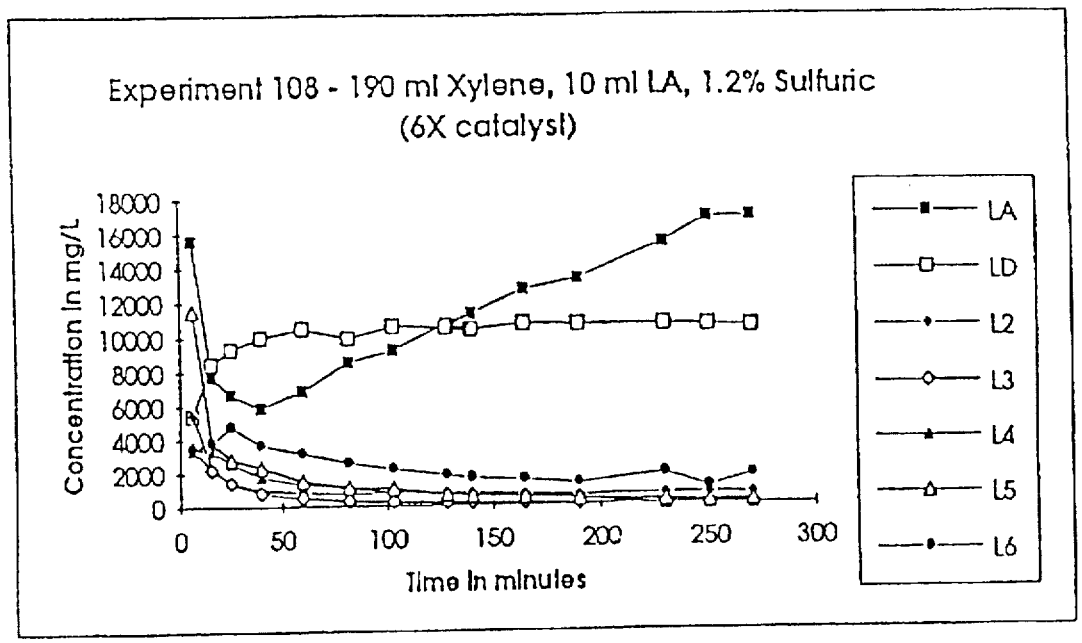
FIG. 4 is a graph showing the production of lactide in xylene using 1.2% sulfuric acid catalyst with the corresponding values for conversion, selectivity and productivity.

A 500 mL round-bottomed three necked flask equipped with a Dean-Stark trap, condenser, thermometer, and sampling septum was charged with 190 mL of xylene and heated to reflux. To the heated solution was added 10 mL of 88% aqueous lactic acid and 1.2% sulfuric acid by weight of XA feed. The reaction mixture was heated at reflux for 2.5 hours. The results of this experiment are illustrated in FIG. 4.

This example illustrates that at a high catalyst concentration of 1.2% sulfuric acid catalyst in a relatively less polar solvent, such as xylene, productivity decreases significantly. This finding is in contrast to the high productivity rates seen at very high catalyst concentrations of up to 10% when a more polar solvent such as anisole is used as is seen in Example 2.

Example 5

This example considers the effect of five different catalysts on productivity, selectivity, and conversion of lactide from lactic acid in anisole.

Figure 5:
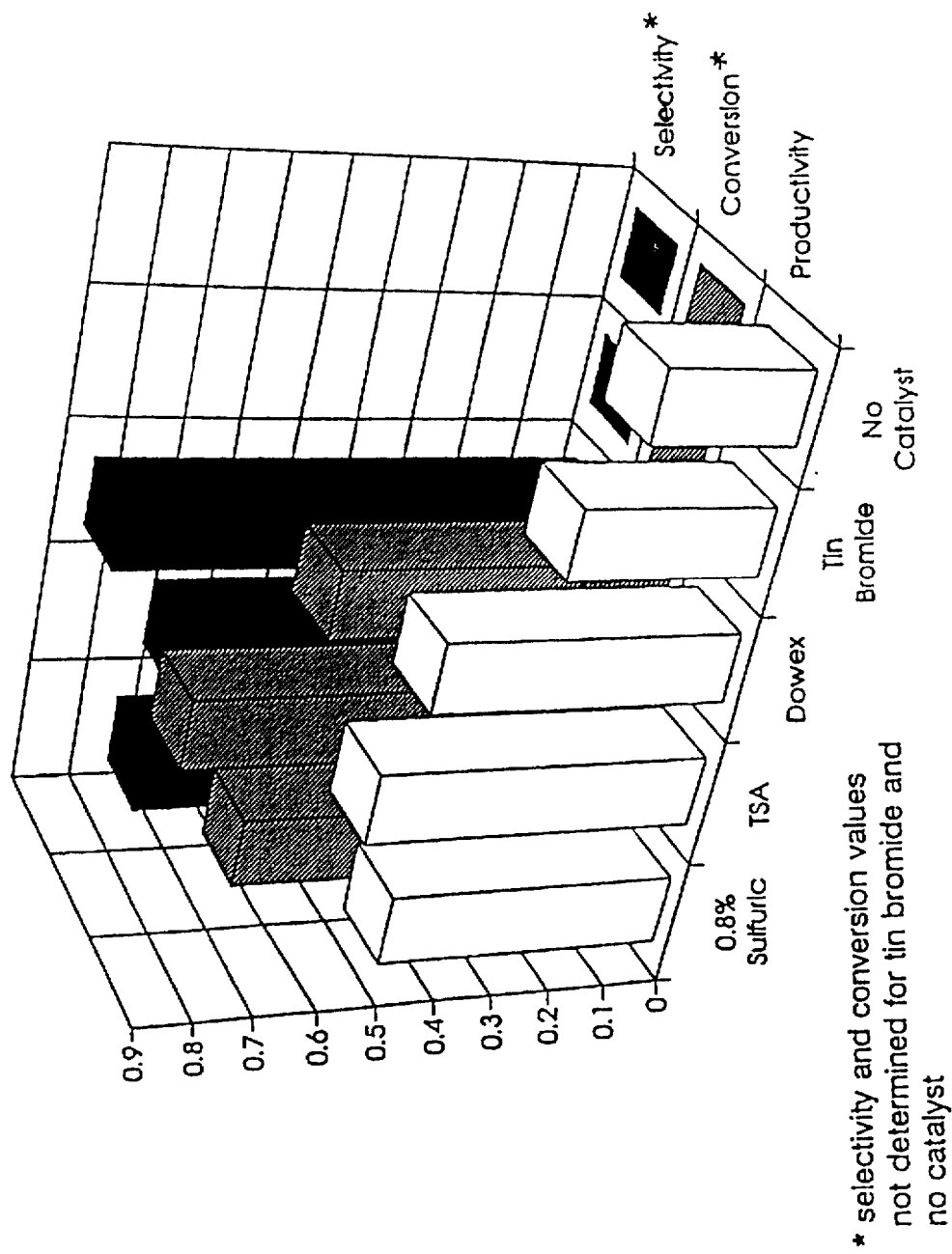
FIG. 5 is a three-dimensional representation of the selectivity, conversion and productivity in the production of lactide in anisole with four different catalysts.

A 500 mL round-bottomed three necked flask equipped with a Dean-Stark trap, condenser, thermometer, and sampling septum was charged with 190 mL of solvent and heated to reflux. To the heated solution was added 10 mL of 88% aqueous lactic acid and catalyst. See Table 5 for catalyst levels. The reaction mixture was heated at reflux for 6 hours. After 315 minutes, a 0.1 mL sample was removed and analyzed for lactide content by HPLC. The results are shown below in Table 5 and illustrated in FIG. 5.

TABLE 5

Effect of Different Catalysts on Lactide Production in Anisole at 315 Minutes

| Catalyst | wt % | Selectivity | Conversion | Productivity |
|---|---|---|---|---|
| Sulfuric Acid | 0.8 | .75 | .65 | .49 |
| Toluene Sulfonic Acid | 1.1 | .72 | .78 | .56 |

TABLE 5-continued

Effect of Different Catalysts on Lactide Production in Anisole at 315 Minutes

| Catalyst | wt % | Selectivity | Conversion | Productivity |
|---|---|---|---|---|
| Dowex | 55.0 | .86 | .58 | .50 |
| Tin bromide | 14.0 | NA* | NA* | .33 |
| None | — | NA* | NA* | .25 |

*Not determined.

The results of this example illustrate that toluene sulfonic acid was the most effective catalyst in terms of conversion and productivity. However, Dowex provided the highest selectivity.

Example 6

This example considers the effect of eight different catalysts on productivity in the production of lactide from lactic acid in anisole.

A 500 mL round-bottomed three necked flask equipped with a Dean-Stark trap, condenser, thermometer, and sampling septum was charged with 190 mL of solvent and heated to reflux. To the heated solution was added 10 mL of 88% aqueous lactic acid and various catalysts. The reaction mixture was heated at reflux for 6 hours. After 300 minutes, a 0.1 mL sample was removed and analyzed for lactide content by HPLC. The results are illustrated below in Table 6.

TABLE 6

Effect of Different Catalysts on Productivity of Lactide Production in Anisole at 300 Minutes

| Catalyst | Productivity |
|---|---|
| Sulfuric Acid (.2%) | .35 |
| Sulfuric Acid (.8%) | .49 |
| Sulfuric Acid (2%) | .50 |
| Sulfuric Acid (10%) | .55 |
| Toluene Sulfonic Acid (1.1%) | .55 |
| Tin Bromide (14%) | .33 |
| Dowex (55%) | .48 |

The results of this example illustrate that the highest productivity is achieved by 1.1% toluene sulfonic acid and 10% sulfuric acid. The 0.8% and 2% sulfuric acid and the Dowex also achieve high productivities.

Example 7

This example illustrates the production of lactide from a lactic acid feed in anisole in a relatively dilute solution at high catalyst concentration.

Figure 6:
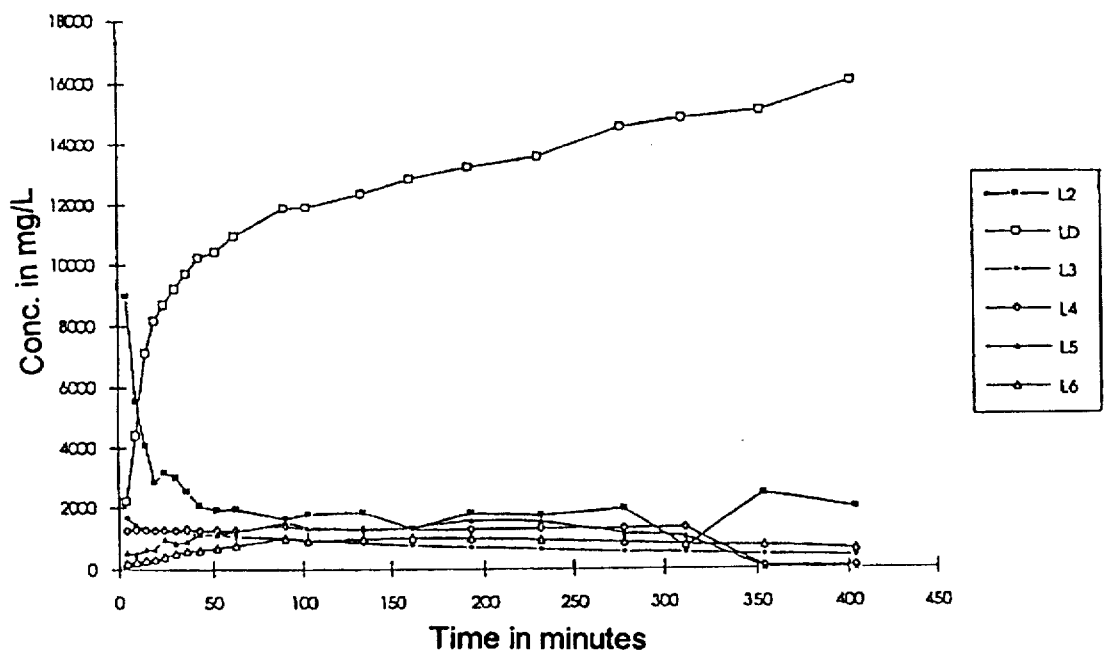
FIG. 6 is a graph showing the production of lactide in anisole at a high catalyst concentration and the corresponding values for conversion, selectivity and productivity.

A 500 mL round-bottomed three necked flask equipped with a Dean-Stark trap, condenser, thermometer, and sampling septum was charged with 190 mL of anisole and heated to reflux. To the heated solution was added 5 mL of 88% aqueous lactic acid and 10% sulfuric acid by weight of XA feed. The reaction mixture was heated at reflux for 6 hours. 0.1 mL samples were removed and analyzed by HPLC over a hour period. The results of this experiment are shown in FIG. 6.

The results of this experiment illustrate that extremely high productivities can be achieved. High selectivity is achieved by use of a highly polar solvent and low feedstream concentration and high conversion is attained by a high catalyst concentration. The productivity at 404 minutes is 81%.

Example 8

This example examines the effect of solvent temperature on lactide production from lactic acid in accordance with the present invention.

Figure 7:
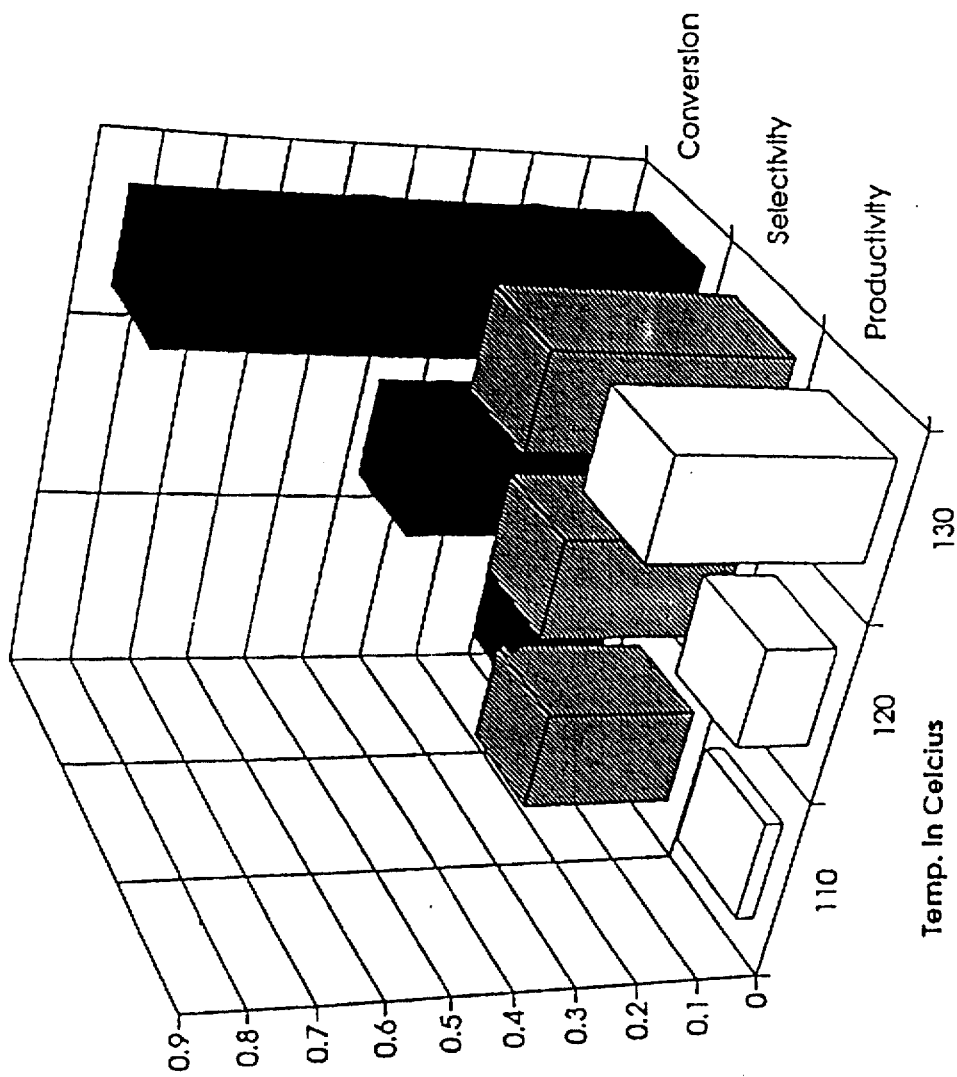
FIG. 7 is a three-dimensional illustration of the conversion, selectivity and productivity in the production of lactide in xylene at three different temperatures.

A 500 mL round-bottomed three necked flask equipped with a Dean-Stark trap, condenser, thermometer, and sampling septum was charged with 190 mL of xylene and heated to reflux. To the heated solution was added 10 mL of 88% aqueous lactic acid and 0.2% sulfuric acid by weight of XA feed. The reaction mixture was heated at reflux for 6 hours. The results of this experiment are shown below in Table 8 and illustrated in FIG. 7.

TABLE 8

Effect of Temperature on Lactide Production in Xylene

| Temperature (C.°) | Selectivity | Conversion | Productivity |
|---|---|---|---|
| 110 | .26 | .15 | .04 |
| 120 | .30 | .44 | .13 |
| 133 | .41 | .88 | .36 |

The results of this experiment illustrate that higher temperatures favor lactide production. This result is believed to be due, in part, to lactic acid being more soluble in the solvent at higher temperatures, and the fact that reaction rate increases at higher temperatures.

Example 9

This example examines the production of lactide using a fed batch reaction process in xylene.

A 500 mL round-bottomed three necked flask equipped with a Dean-Stark trap, condenser, thermometer, and sampling septum was charged with 190 mL of xylene and heated to reflux. To the heated solution was added a mixture of 45 mL of 88% aqueous lactic acid and 0.2% sulfuric acid by weight of XA feed in nine 5 mL increments over 400 minutes. 0.1 mL samples were removed at 25 minute intervals and analyzed for lactide content by HPLC. The results are presented in FIG. 8.

Figure 8:
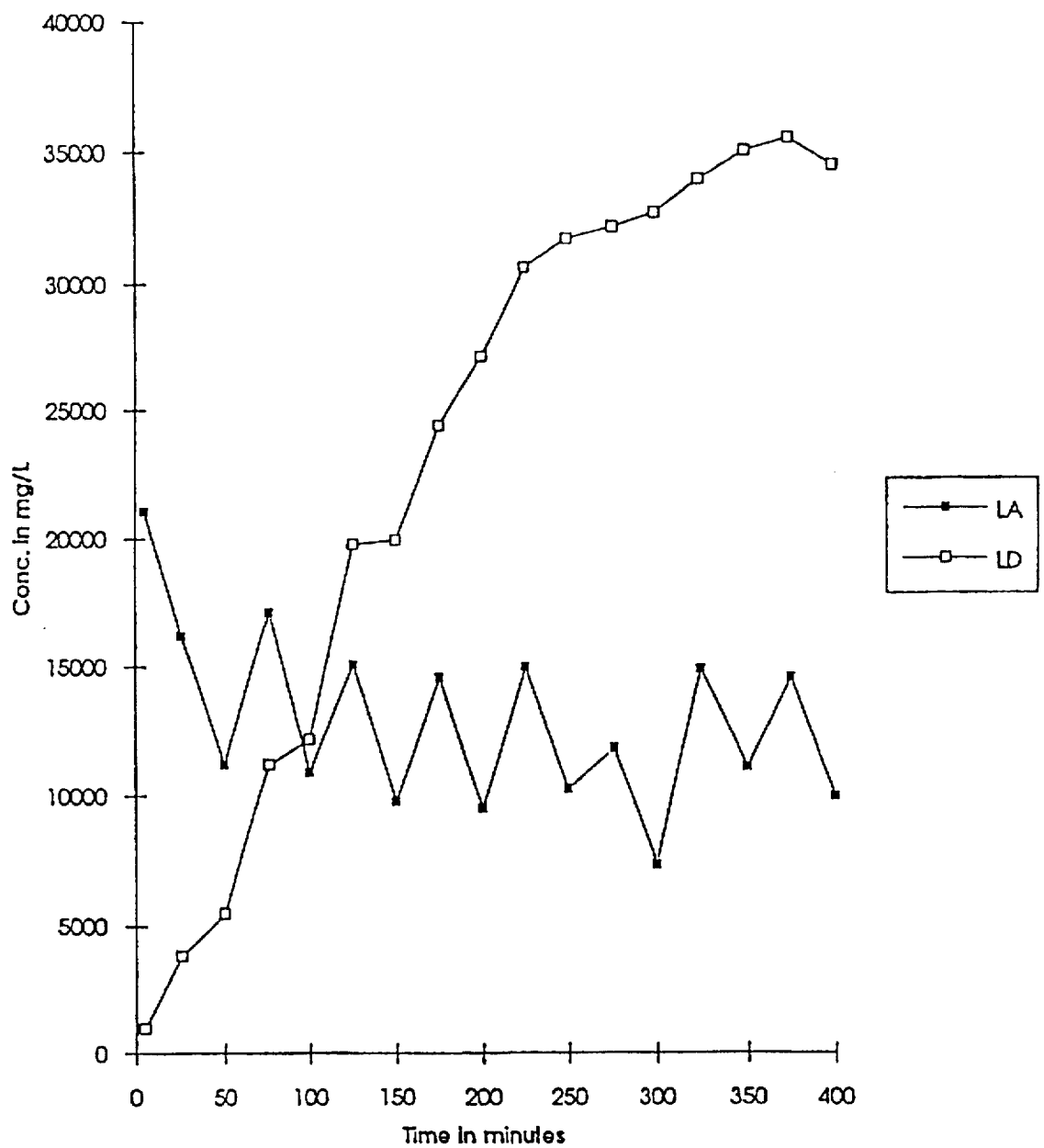
FIG. 8 is a graph showing the production of lactide in xylene in a fed batch production process.

FIG. 8 shows a linear increase of lactide formation up to 30,000 mg/L. The results of this example illustrate that fed batch production of lactide is feasible. In operation, a lactide production operation would require the recovery of lactide from the reaction vessel at concentrations less than this maximum value to insure continuous lactide production.

Example 10

This example examines the production of lactide using a fed batch reaction process in anisole.

A 500 mL round-bottomed three necked flask equipped with a Dean-Stark trap, condenser, thermometer, and sampling septum was charged with 190 mL of anisole and heated to reflux. To the heated solution was added a mixture of 45 mL of 88% aqueous lactic acid and 0.2% sulfuric acid by weight of XA feed in nine 5 mL increments over 400 minutes. 0.1 mL samples were removed at 25 minutes intervals and analyzed for lactide content by HPLC. The results are presented in FIG. 9.

Figure 9:
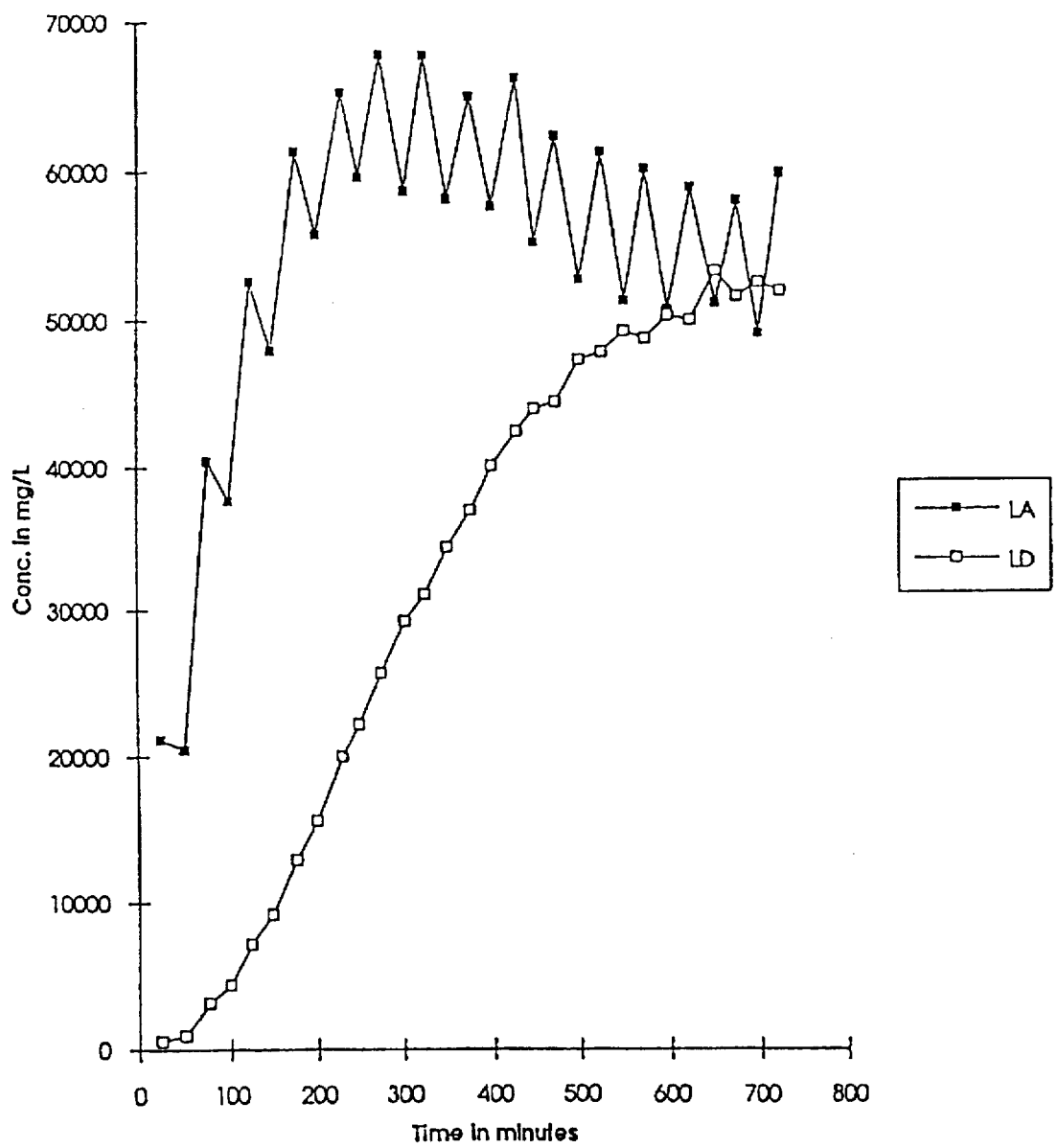
FIG. 9 is a graph showing the production of lactide in anisole using a fed batch production process.

FIG. 9 shows that when anisole is used, formation of lactide is linear up to 50,000 mg/L after which it levels off. The results of this example illustrate that fed batch production of lactide is feasible. In operation, a lactide production operation would require the recovery of lactide from the reaction vessel at concentrations less than this maximum value to insure continuous lactide production.

Example 11

This example examines this use of mixed solvents using polar and non-polar solvents and the effect on production, conversion, and selectivity of lactide formation from lactic acid. Three solvent ratio's were chosen to demonstrate the effect of mixed solvent combinations.

A 500 mL round-bottomed three necked flask equipped with a Dean-Stark trap, condenser, thermometer, and sampling septum was charged with 190 mL of mixed solvent which contained either 10, 20, or 30% by volume anisole in xylene. The mixed solvent solution was heated to reflux temperature. 10 mL of 88% aqueous lactic acid and 0.2% sulfuric acid were added to the refluxing solution and heating was continued for 375 minutes. 0.1 mL samples were removed every 40 minutes and analyzed for lactide content by HPLC. The results comparing the three mixtures in terms of conversion, selectivity and productivity are presented in FIGS. 10, 11, and 12, respectively.

Figure 10:
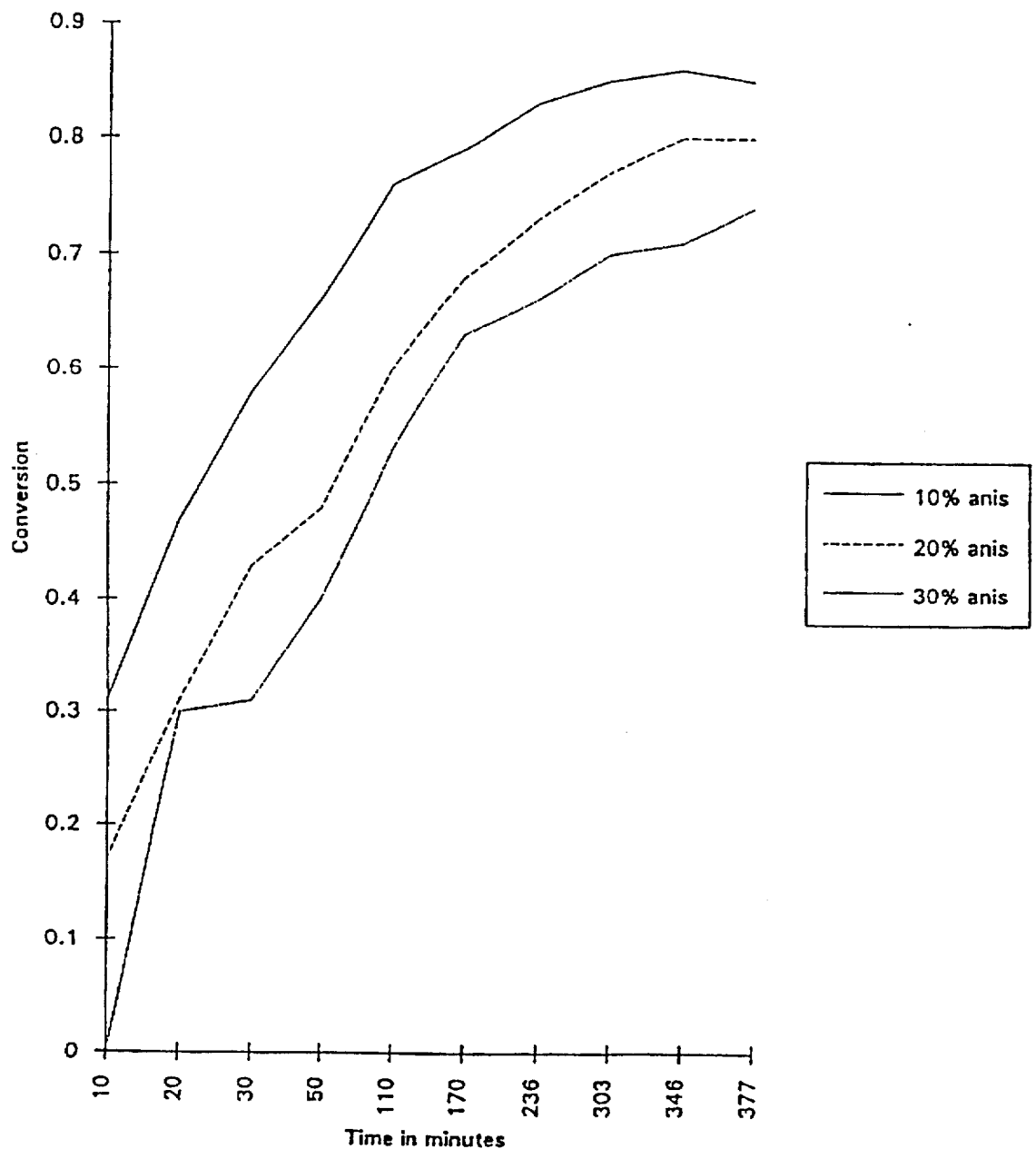
FIG. 10 is a graph showing the results of lactide production in a mixed anisole/xylene solvents in terms of conversion.
Figure 11:
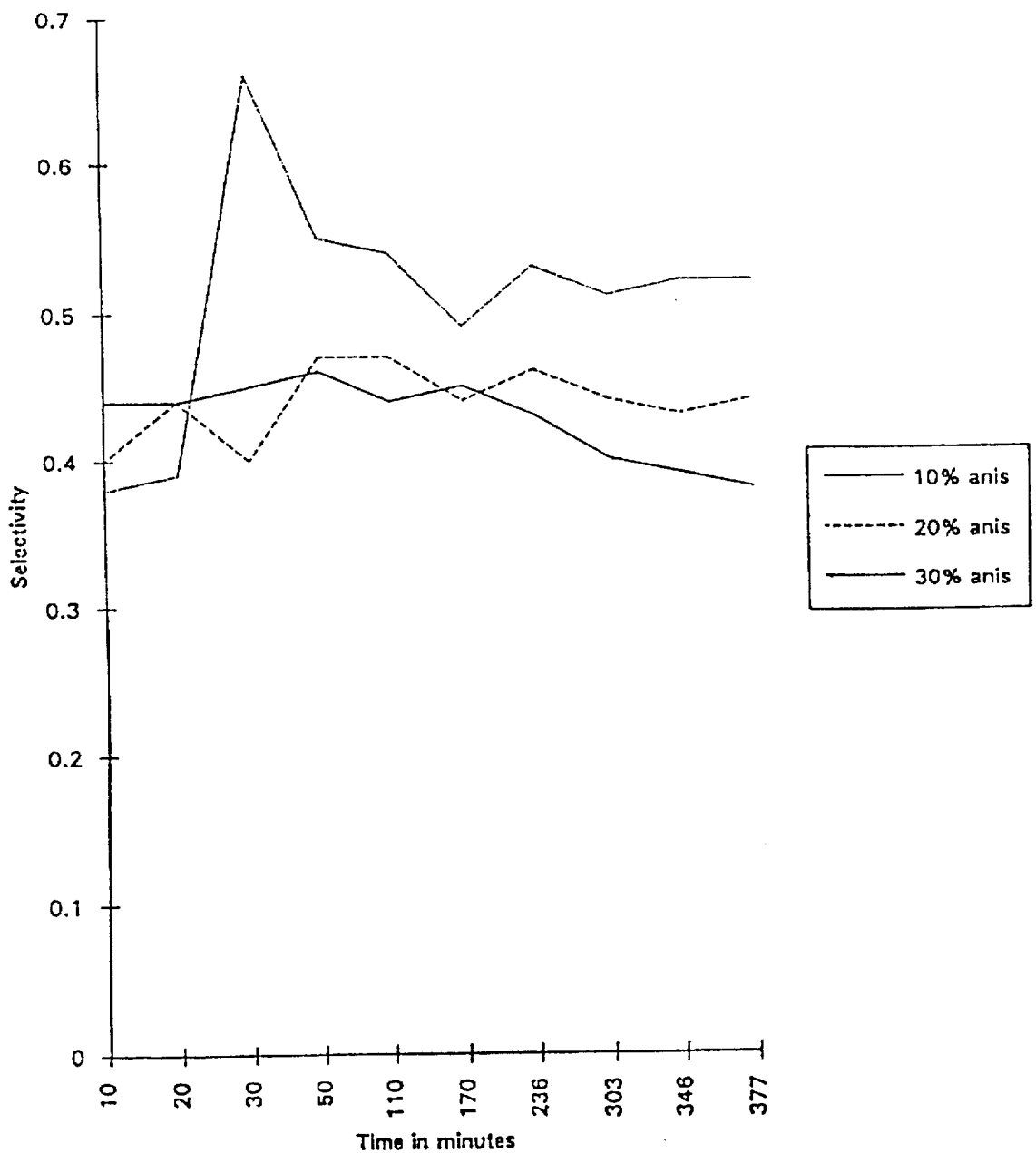
FIG. 11 is a graph showing the results of lactide production in mixed anisole/xylene solvents in terms of selectivity.
Figure 12:
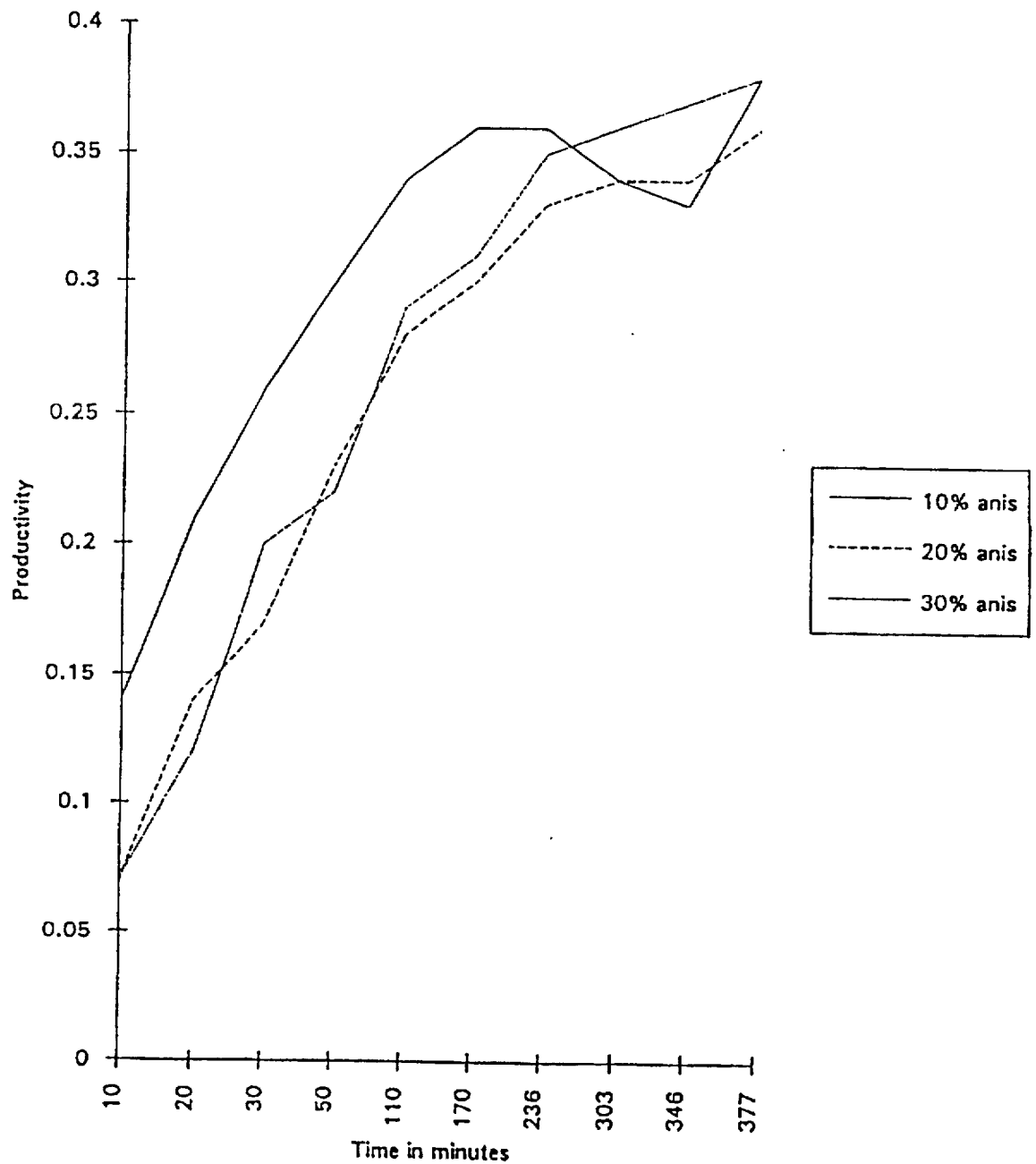
FIG. 12 is a graph showing the results of lactide production in mixed xylene/anisole solvents in terms of productivity.

FIG. 10 illustrates that the percent conversion of lactic acid to lactide is enhanced by higher concentrations of xylene in the mixed solvent medium, although all three mixed solvents achieve relatively high conversion rates. FIG. 11 illustrates that selectivity for lactide formation is increased as the mixed solvent system has increased anisole concentrations. FIG. 12 demonstrates that the three mixed solvents have approximately equivalent productivities under the reaction conditions.

Example 12

This example examines various combinations of nine cyclic ester production solvents in terms of twelve catalysts and their conversion, selectivity and productivity in the production of lactide. Solvents chosen represent a wide range of boiling points, azeotrope concentrations, and ionic strength. Four classes of solvents were examined: ethers, ketones, aromatics and alkanes. Catalysts were chosen to investigate different catalytic mechanisms for lactide productivity and selectivity. These included homogeneous acid catalysts, mineral surface catalysts, metal catalysts, amine base catalysts, and template catalysts. The solvents and catalysts are identified in Tables 12.1 and 12.2.

TABLE 12.1

| Solvents | Designation |
|---|---|
| Isopropyl Ether | A |
| 2-Pentanone | B |
| Toluene | C |
| Octane | D |
| Xylene | E |
| Butyl Ether | F |
| Anisole | G |
| 2-Octanone | H |
| Dimethyl sulfoxide | I |

TABLE 12.2

| Catalysts | Designation | Amounts |
|---|---|---|
| Dowex 50 | 1 | 0.025 g |
| Nafion NR50 | 2 | 0.1625 g |
| Alumina, Brockmann I | 3 | 0.1 g |
| Zn dust | 5 | 0.0026 g |
| Sn dust | 6 | 0.0047 g |
| LiBr | 7 | 0.0204 g |
| MgSO$_2$ | 8 | 0.0282 g |

TABLE 12.2-continued

| Catalysts | Designation | Amounts |
|---|---|---|
| SnBr$_2$ | 9 | 0.0653 g |
| H$_2$SO$_4$ | 10 | 0.18 mol % |
| p-toluene sulfonic acid | 11 | 0.18 mol % |
| pyridine | 12 | 7.5 vol % |
| Phosphoric acid | 13 | 0.18 mol % |
| No catalyst | 14 | ... |

A 40 mL glass sample vial was charged with catalyst, 9.5 mL of solvent, and 0.5 mL 88% lactic acid. Catalyst amount and solvent are identified in Tables 12.1 and 12.2. A 12 inch by 1.5 inch diameter piece of glass tubing was sealed to the vial. A cone made of qualitative filter paper was set on top of the vial and filled with approximately 2 grams of sodium sulfate. The vial and the contents were heated in an oil bath to a temperature slightly above the boiling temperature of the solvent. During the experiment, the vials were topped off with solvent to maintain a constant volume. Each run consisted of one solvent, all catalysts and sample times of one and four hours. For each sample time, an aliquot of approximately 0.5 mL was taken directly from the vial as soon as the apparatus was removed from the hot oil bath. Samples were analyzed by high performance liquid chromatography for lactic acid, lactide, and oligomers of up to 6 lactic acid repeat units.

Figure 13:
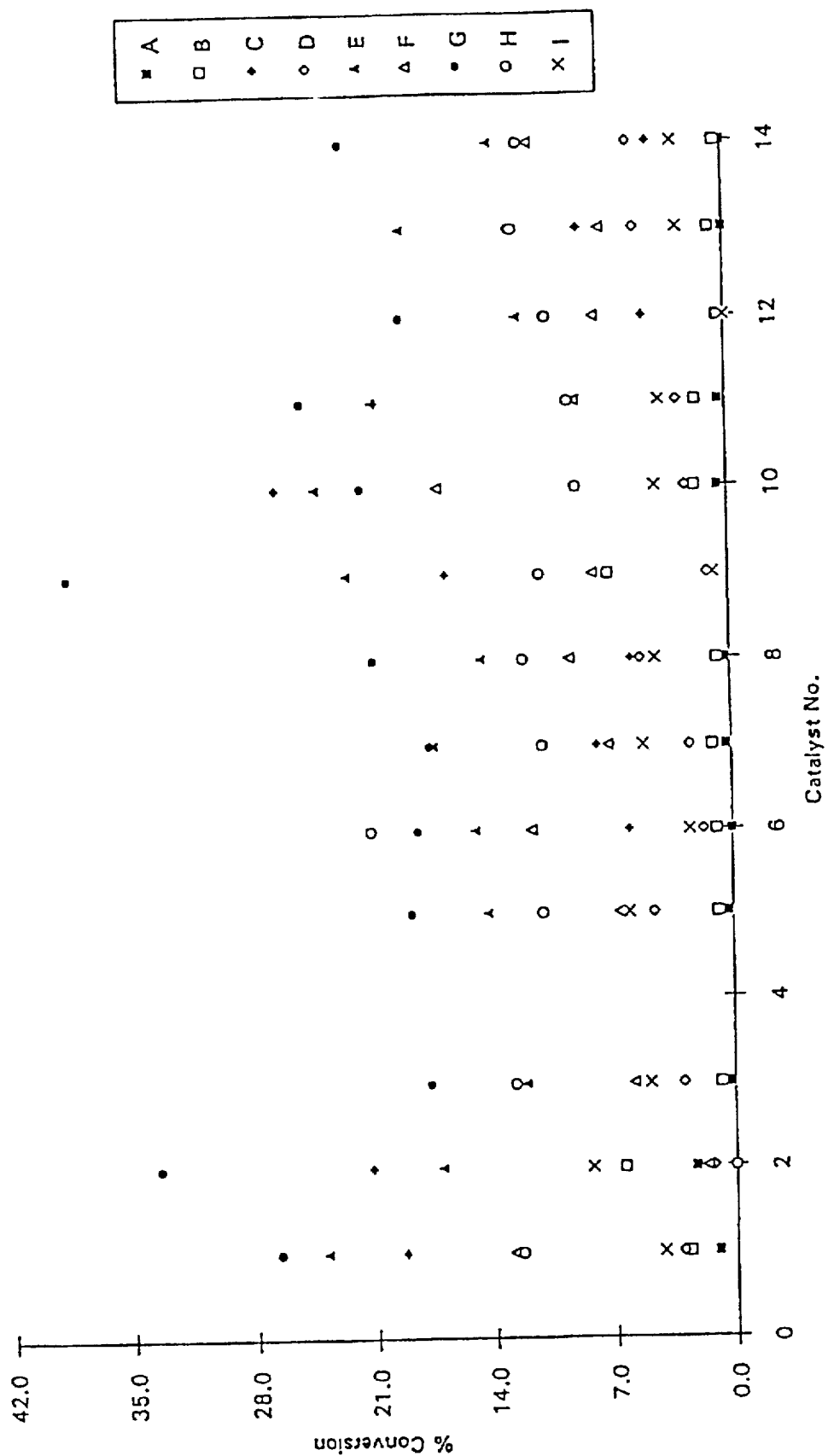
FIG. 13 is a graph showing the percent conversion in a lactide synthesis reaction using a variety of solvent and catalyst combinations after four hours.
Figure 14:
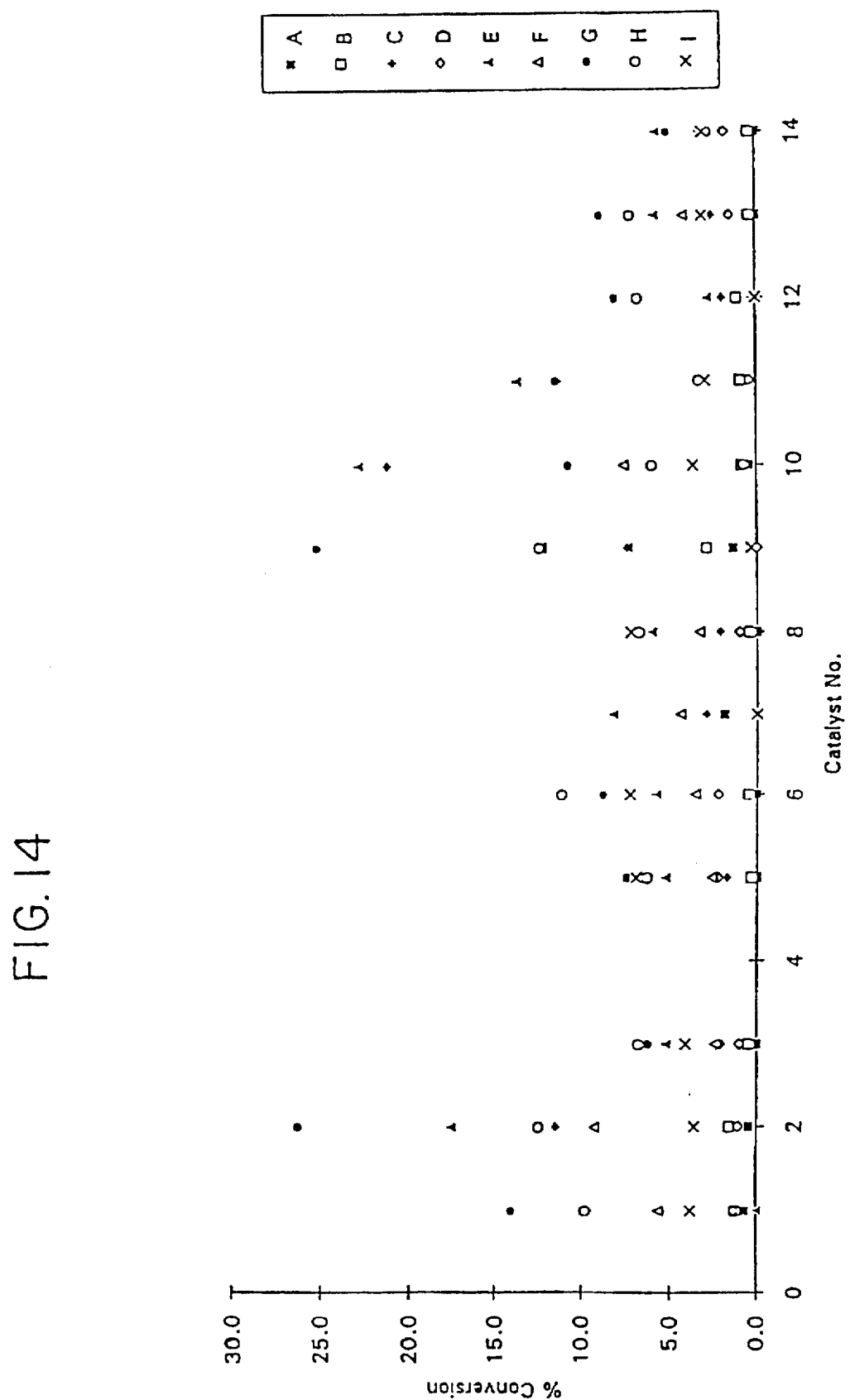
FIG. 14 is a graph showing the percent conversion in a lactide synthesis reaction for a variety of solvent and catalyst combinations after one hour.

FIGS. 13 and 14 show conversion after four hours and one hour for each of the solvent/catalyst combinations. The combinations of anisole as solvent and either SnBr$_2$ or Nafion as catalyst are the best combinations with conversion of almost 39% in the four hour run and 26% in the one hour run. In addition, H$_2$SO$_4$, Dowex, Nafion and SnBr$_2$ were all successful catalysts. Anisole, toluene and xylene worked well as solvents. In general, within a class of solvents for which more than one solvent was tested (ethers, ketones, and aromatics), higher boiling point solvents produced higher conversion.

Figure 15:
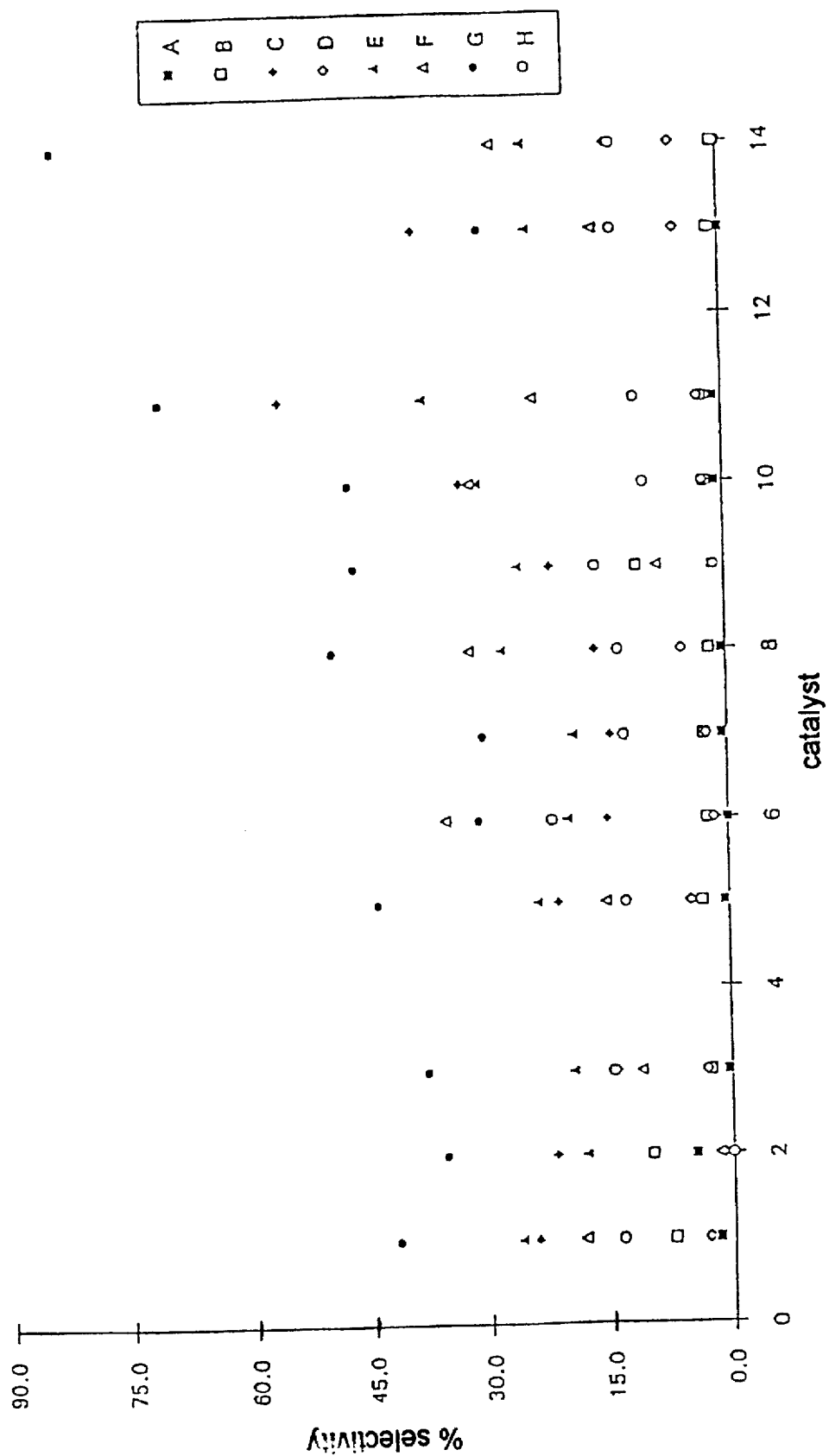
FIG. 15 is a graph showing the selectivity of lactide formation using a variety of solvent and catalyst combinations.

The results in FIG. 15 show that anisole and toluene had the highest selectivity, with xylene and butyl ether having high selectivity as well. p-Toluenesulfonic acid appears to be the most selective catalyst. MgSO$_4$, SnBr$_2$ and H$_2$SO$_4$ also provide high selectivity.

Example 13

The following example examines the effect on cyclic ester productivity and efficiency of using a variety of reaction configurations. The reaction configurations are described below as Runs 13.1–13.6. Various operating parameters and the results are provided in Table 13. In the following examples, catalyzed lactic acid refers to 88% lactic acid charged with 0.1% sulfuric acid by weight of lactic acid feed.

Run 13.1: Four Staged CSTRs

Four 500 mL three-necked round-bottomed flasks, equipped with reflux condensers, Dean-Stark traps, and sample ports were connected in line via tubing. Each flask was charged with 180 g of xylene with all flasks charged with 20 g of catalyzed lactic acid. The flasks were heated to reflux temperature for 1 hour at which point xylene and catalyzed lactic acid were fed into the first flask at a feed rate of 360 g/h xylene and 40 g/h catalyzed lactic acid. The reaction medium from the first flask was fed to the adjacent flask and so forth until solution containing lactide was removed from the fourth flask at a rate equal the addition of xylene and lactic acid to the first flask.

Run 13.2: One Foot Column and Two CSTRs

A 500 mL 3-necked round-bottomed flask was equipped with a 1 foot column packed with 5 mm Rashing rings. The packed column was fitted with a Dean-Stark trap, reflux condenser and a heating jacket. Through the top of the heated column was added 40 g/h of catalyzed lactic acid. The resultant lactic acid, free of water, cascaded down the column into 300 mL of refluxing xylene. Xylene was added to the reaction vessel at a rate of 440 g/h with removal of solution containing product at an equivalent rate so as to maintain a working volume of approximately 300 mL in the first flask. The solution from the first 3-necked flask was fed into a second 1000 mL round-bottomed flask charged with 700 mL of refluxing xylene equipped with a reflux condenser and Dean-Stark trap. Removal of solution containing lactide product from the second flask was done at a rate to maintain a constant volume in the reaction flask. The first flask was charged with 20 g catalyzed lactic acid and the second flask was charged with 60 g catalyzed lactic acid.

Run 13.3: Four Foot Packed Column and One CSTR

A 500 mL 3-necked round bottomed flask was equipped with a 4 foot column packed with 5 mm Rashing rings. The packed column was fitted with a Dean-Stark trap, reflux condenser and a heating jacket. The flask was charged with 25 g of catalyzed lactic acid. Through the top of the heated column was added 25 g/h of catalyzed lactic acid. The resultant lactic acid, free of water, cascaded down the column into 300 mL of refluxing xylene. Xylene was added to the reaction vessel at a rate of 230 g/h with removal of solution containing product at an equivalent rate so as to maintain a working volume of approximately 300 mL.

Run 13.4: Two Foot Packed Column and One CSTR

A 1000 mL 3-necked round bottomed flask was equipped with a 2 foot column packed with 5 mm Rashing rings. The packed column was fitted with a Dean-Stark trap, reflux condenser and a heating jacket. The flask was charged with 25 g of catalyzed lactic acid. Through the top of the heated column was added 25 g/h of catalyzed lactic acid. The resultant lactic acid, free of water, cascaded down the column into 500 mL of refluxing xylene. Xylene was added to the reaction vessel at a rate of 460 g/h with removal of solution containing product at an equivalent rate so as to maintain a working volume of approximately 500 mL.

Run 13.5: Perforated Plate Column and One CSTR

A 1000 mL round-bottomed 3 necked flask was equipped with a 40 inch×3 inch outside diameter vacuum jacketed perforated plate column, an insulated heat jacketed 2 inch by 18 inch column filled with 5 mm Raschig rings attached to the top of the column, a reflux condenser, a Dean-Stark trap, and charged with 800 mL of xylene. The system was refluxed for 1 hour prior to addition of lactic acid solution to equilibrate the column. A minimum reflux of about 1400 g/h xylene was necessary to maintain the liquid hold-up on the trays in the perforated column. The flask was charged with 80 g of catalyzed lactic acid. Through the top of the heated column was added 80 g/h of catalyzed lactic acid. The resultant lactic acid, free of water, cascaded down into the perforated plate column into the vaporized/refluxing xylene. Xylene was added to the reaction vessel at a rate of 400 g/h with removal of solution containing product at an equivalent rate so as to maintain a working volume of approximately 1000 mL.

Run 13.6: Perforated Plate Column and One CSTR

A 2000 mL round-bottomed 3 necked flask was equipped with a 40 inch×3 inch outside diameter vacuum jacketed perforated plate column, an insulated heat jacketed 2 inch by 18 inch column filled with 5 mm Raschig rings attached to the top of the vacuum column, a reflux condenser, a Dean-Stark trap, and charged with 1000 mL of xylene. The system was refluxed for 1 hour prior to addition of lactic acid solution to equilibrate the column. A minimum reflux of about 1400 g/h xylene was necessary to maintain liquid hold-up in the trays of the perforated column. The flask was charged with 180 g of catalyzed lactic acid. Through the top of the heated column was added 180 g/h of catalyzed lactic acid. The resultant lactic acid, free of water, cascaded down into the perforated plate column into the vaporized/refluxing xylene. Xylene was added to the reaction vessel at a rate of 820 g/h with removal of product containing solution at an equivalent rate so as to maintain a working volume of approximately 1150 mL.

TABLE 13

| Run | Stage/column | $L_1A$ conc. (%) | Residence time column (min.) | Residence time total (h) | $L_1A$ - conversion | LD - selectivity | LD - productivity | Solvent | Efficiency (g/l/hr.) |
| --- | --- | --- | --- | --- | --- | --- | --- | --- | --- |
| 13.1 | 4/no column | 7.7 | — | 1.9 | 0.84 | 0.45 | 0.37 | xylene | 13.4 |
| 13.2 | 2/1 ft. column | 7.7 | 3 | 1.9 | 0.85 | 0.45 | 0.39 | xylene | 13.9 |
| 13.3 | 1/4 ft. column | 8.8 | 10 | 1.0 | 0.82 | 0.46 | 0.38 | xylene | 27.3 |
| 13.4 | 1/2 ft. column | 4.1 | 5 | 1.1 | 0.72 | 0.55 | 0.40 | xylene | 13.0 |
| 13.5 | per. plate column | 16.6 | 15 | 1.7 | 0.82 | 0.47 | 0.39 | xylene | 38.1 |
| 13.6 | per. plate column | 14.1 | 15 | 1.0 | 0.82 | 0.40 | 0.33 | xylene | 48 |

Efficiency = L1A concentration in system × Productivity/Residence time

The foregoing results demonstrate that high productivity and efficiency can be achieved by use of staged reactor configurations. In particular, efficiency can be increased significantly at high column residence times. The distillation columns increased overall reaction rates due to increased mass and heat transfer achieved in the column as compared to the CSTR's. The increased mass and heat transfer maintained water content in the liquid phase at low levels which drives the reaction to more complete esterification and minimized competing back reactions.

Example 14

This example demonstrates preparation of the cyclic diester of α-hydroxyisobutyric acid.

In 200 mL of an organic solvent of 10% by weight anisole and 90% by weight xylene is dissolved commercially available α-hydroxyisobutyric acid feed. The resulting mixture has approximately 5% by weight α-hydroxyisobutyric acid feed with the remainder being solvent. From about 0.2% to about 2.0% by weight of sulfuric acid, relative to the α-hydroxyisobutyric acid, is added to the mixture. The mixture is heated to a boil and vapor is refluxed while water from the vapor is collected in a Dean-Stark trap. A sample taken from the mixture after several hours of such refluxing is analyzed by high performance liquid chromatography (HPLC). HPLC with mass spectrometry detection shows the presence of the cyclic diester of α-hydroxyisobutyric acid in the sample.

Example 15

This example demonstrates preparation of the cyclic diester of α-hydroxyisovaleric acid.

A mixture having about 5% by weight of commercially available α-hydroxyisovaleric acid dissolved in 200 mL of xylene is prepared in the manner as described in Example 1. A small amount of sulfuric acid (from about 0.2% to about 2% by weight relative to α-hydroxyisovaleric acid) is added to the mixture. The mixture is heated to a boil and vapor is refluxed while water from the vapor is collected in a Dean-Stark trap as described in Example 14. A sample taken from the mixture after several hours of such reflux shows the presence of the cyclic diester of α-hydroxyisovaleric acid, using HPLC with mass spectrometry.

Examples 16–18

Cyclic diesters of α-hydroxycaproic acid, α-hydroxyisocaproic acid and α-hydroxyoctanoic acid are prepared in xylene according to the procedure of Example 15. Commercially available α-hydroxycarboxylic acids are used as feed for each of the respective tests. Analyzing samples by HPLC with mass spectrometry shows that the cyclic diesters are prepared.

Example 19

This example demonstrates preparation and purification of the cyclic diester of α-hydroxyoctanoic acid. To a three-neck flask fitted with a heating mantel, pot thermometer, magnetic stirrer, Dean-Stark trap, reflux condenser and a rubber septum is added approximately 5 g of α-hydroxyoctanoic acid, 95 mL of toluene and 0.22 g of Dowex-50™ catalyst (available from Dow Chemical). The mixture was heated to reflux (approximately 116° C.), and aliquots were taken at various time intervals over 48 hours. The aliquots were derivatized with diazomethane. Gas chromatography/mass spectrometry shows the presence of the cyclic diester of α-hydroxyoctanoic acid in samples taken at 1, 29 and 48 hours of reflux.

Cyclic diester remaining in the reaction mixture at the end of the experiment is isolated from the feed α-hydroxyoctanoic acid using an ion exchange resin (Amberlyst™ A-21 available from Rohm & Haas) from about 200 to about 300 mL of the ion exchange resin was placed in a 1 inch inner diameter chromatography column. A 1:1 toluene/acetone solution (by volume) is prepared and used to treat the ion exchange resin until effluent from the resin is neutral. A sample of the reaction mixture is then diluted 1:1 with acetone (by volume) and the diluted reaction mixture is passed over the resin and the eluate is recovered. Analysis of the eluate shows that it is predominantly composed of the cyclic diester of α-hydroxyoctanoic acid. Based on the amount of cyclic ester in the eluate, the yield of isolated cyclic ester is approximately 15%.

Example 20

This example demonstrates production of the cyclic ester of α-hydroxyoctanoic acid using a mesitylene (1,3,5-trimethlybenzene) solvent. Three experiments are performed using α-hydroxyoctanoic acid concentrations in mesitylene of 20%, 10%, and 5% (wt./vol.) respectively. Reaction mixtures were heated at reflux for 5.5 hours according to the procedure of Example 19. Aliquots were periodically taken throughout the course of each reaction and samples were derivatized and analyzed by gas-chromatography. The 20% solution gave the highest yields of cyclic esters, peaking at between about 25 and 30% yield at 2.5 to 3.5 hours of reflux. Yields in the 10% solution peaked at about 25% at about 3.5 hours of reflux. Yields in the 5% solution reached about 15% after 5.5 hours.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A process for the recovery of cyclic ester from a cyclic ester production mixture, wherein said cyclic ester production mixture comprises cyclic esters, a compound selected from the group consisting of a single hydroxycarboxylic acid or its ester, salt or amide ($X_1A$) and oligomers of $X_1A$, said process comprising:

(a) providing a recovery solvent for said cyclic ester production mixture;
   (b) separating at least a portion of said cyclic esters and recovery solvent from $X_1A$ and oligomers of $X_1A$ by liquid-liquid equilibrium separation; and
   (c) recovering cyclic esters from said cyclic ester and recovery solvent.

2. The process of claim 1, wherein said cyclic ester has a separation factor with respect to $X_1A$ in the recovery solvent at about room temperature at 1 atm of at least about 1.

3. The process of claim 1, wherein said recovery solvent is selected from the group consisting of xylene, toluene, benzene, methyl isobutyl ketone, isopropyl ether and mixtures thereof.

4. The process of claim 1, further comprising conducting solvent extraction on said $X_1A$ and oligomers of $X_1A$ with additional solvent to recover additional cyclic ester therefrom.

5. The process of claim 4, wherein said additional solvent comprises said recovery solvent.

6. The process of claim 1, wherein said step of separating is selected from the group consisting of allowing phase separation and reflux extraction.

7. The process of claim 1, further comprising removing recovery solvent prior to said step of recovering.

8. The process of claim 1, wherein said $X_1A$ comprises lactic acid and said cyclic esters comprise lactide.

9. The process of claim 1, wherein said cyclic esters were produced in a solution comprising said recovery solvent.

10. The process of claim 1, wherein said cyclic esters were produced in a solution comprising a mixture of said recovery solvent and a solvent more polar than said recovery solvent.

11. The process of claim 1, wherein said step of recovering comprises a process selected from the group consisting of distillation, solvent crystallization, melt crystallization and mixtures thereof.

12. The process of claim 1, wherein said cyclic ester production mixture is produced by a process comprising:
   (a) providing a feedstream comprising XA, wherein XA comprises $X_1A$; a straight chain two member molecule of $X_1A$ ($X_2A$); a straight chain three member molecule of $X_1A$ ($X_3A$); a straight chain four member molecule of $X_1A$ ($X_5A$); a straight chain five member molecule of $X_1A$ ($X_5A$); and mixtures thereof in a production solvent; and
   (b) removing water from said feedstream and forming said cyclic esters, wherein the concentration of $X_5A$ and higher oligomers formed from the feedstream is less than about 20 wt % of the reaction mixture during said process.

13. The process of claim 12, wherein said recovery solvent comprises said production solvent.

14. A process for the purification of cyclic ester from a cyclic ester mixture, wherein said cyclic ester mixture comprises cyclic ester, a compound selected from the group consisting of a single hydroxycarboxylic acid or its ester, salt or amide ($X_1A$), oligomers of $X_1A$ and solvent, said process comprising:
   (a) selectively distilling at least a portion of said $X_1A$ and solvent from said cyclic ester mixture to form a mixture of cyclic ester and oligomers of $X_1A$;
   (b) selectively distilling at least a portion of cyclic ester from mixture of cyclic ester and oligomers of $X_1A$;
   (c) recovering said distilled cyclic ester by a technique selected from the group consisting of solvent crystallization, melt crystallization and mixtures thereof.

15. The process of claim 14, wherein at least one of said steps of distillation is conducted under less than atmospheric pressure.

16. A process for the purification of cyclic ester from a cyclic ester mixture, wherein said cyclic ester mixture comprises first and second isomeric species of cyclic ester, a compound selected from the group consisting of a single hydroxycarboxylic acid or its ester, salt or amide ($X_1A$) and oligomers of $X_1A$, said process comprising:
   (a) selectively solvent crystallizing said first isomeric species of said cyclic ester;
   (b) recovering said solvent crystallized first isomeric species of said cyclic ester;
   (c) crystallizing said second isomeric species of said cyclic ester; and
   (d) recovering said crystallized second isomeric species of said cyclic ester.

* * * * *